(12) United States Patent
Szmuszkovicz et al.

(10) Patent No.: US 6,436,954 B1
(45) Date of Patent: Aug. 20, 2002

(54) BENZOQUINOLIZIDINE AND BENZOINDOLIZIDINE DERIVATIVES AND THERAPEUTIC USES THEREOF

(75) Inventors: Jacob Szmuszkovicz, Kalamazoo, MI (US); Ciaran Regan, Dublin (IE)

(73) Assignees: American Biogenetic Sciences, Inc., Copiague, NY (US); University College Dublin, Dublin (IE)

( * ) Notice: Subject to any disclaimer, the term of this patent is extended or adjusted under 35 U.S.C. 154(b) by 0 days.

(21) Appl. No.: 09/744,183

(22) PCT Filed: Jul. 20, 1999

(86) PCT No.: PCT/US99/16432

§ 371 (c)(1),
(2), (4) Date: Mar. 14, 2001

(87) PCT Pub. No.: WO00/04905

PCT Pub. Date: Feb. 3, 2000

Related U.S. Application Data

(60) Provisional application No. 60/093,617, filed on Jul. 21, 1998.

(51) Int. Cl.[7] ..................... A61K 31/473; C07D 455/04
(52) U.S. Cl. ......................... 514/294; 514/290; 546/94
(58) Field of Search ............................. 546/79, 94, 95; 514/290, 294

(56) References Cited

U.S. PATENT DOCUMENTS 3,565,899 A  2/1971  Doebel et al. .............. 260/286
3,824,244 A  7/1974  Houlihan et al. ........... 260/295

OTHER PUBLICATIONS

Jeffrey Watthey et al J.Org. Chem vol. 38 4170–4172 Jun. 1973.*

C.K. Bradsher et al J. Org. Chem. vol. 38 pp. 4167–4170. Jun. 1973.*

Kupchan et al. Hydrobenzo[b]quinolizines. II. the synthesis and sterochemistry of derivatives of 1,3,4, 11a —Tetrahydro–8,9–dimethoxy–2H–benzo[b]quinolizin–11(6H)–o ne. J. Org. Chem. Jun. 1996, vol. 31 pp. 1713–1716, especially p. 17113, compounds 5,7.

Chem. Abst., vol. 99 No. 23, Dec. 5, 1983, p. 738 col. 2, the abstract No. 194796b,.

Knefeli et al. 'Electron–impact induced loss of C–5 and C–8 substituents in 1,2,3,4–tetrahydroisoquinolines. I. Synthesis of 4–acetylpyrrolo[1,2–b]isoquinoline.' Arch. Pharm. (Weinheim, Ger.) 1983, 316 (9), 773–81 (Ger.).

* cited by examiner

Primary Examiner—Alan L. Rotman
Assistant Examiner—Rita Desai
(74) Attorney, Agent, or Firm—Morgan & Finnegan, LLP

(57) ABSTRACT

Benzo[b]quinolizidine and benzo[f]indolizidine derivatives are provided which are useful for the treatment of Alzheimer's disease, senile dementia or other conditions characterized by memory loss. Pharmaceutical compositions containing these compounds, and methods for their use, are also provided.

10 Claims, No Drawings

US 6,436,954 B1

BENZOQUINOLIZIDINE AND BENZOINDOLIZIDINE DERIVATIVES AND THERAPEUTIC USES THEREOF

This application is a 371 of PCT/US99/16432 filed Jul. 20, 1998 and claim priority to provisional 60/093,617 filed Jul. 21, 1998.

FIELD OF THE INVENTION

This invention relates to benzo[b]quinolizidines, be U[f] indolizidines, and ring-expanded derivatives thereof, which are useful for the treatment of neurodegenerative states and diseases associated with memory impairment. The invention also relates to pharmaceutical compositions comprising these compounds, and to methods of treating or controlling the symptoms of Alzheimer's disease, senile dementia, or other conditions associated with the impairment of memory. The compounds of this invention are weak inhibitors of neural acetylcholinesterase in vitro. The compounds of this invention also protect rodents against scopolamine-induced amnesia without inducing psychomotor or behavioral deficits.

BACKGROUND OF THE INVENTION

Impairment of cognition and memory is associated with numerous diseases. The most widely known is Alzheimer's disease, which is associated with extensive loss of specific neuronal subpopulations in the brain (Sims, N. R., et al. (1987) *Annals of Neurology* 21:451; Katzman, R. (1986) *New England Journal of Medicine* 314:964). The biochemical and cellular changes which lead to neuronal loss remain unknown. Proposed causes include environmental factors, (Perl, D. P. (1985) *Environmental Health Perspective* 63:149; Katzman, R. (1986)), including metal toxicity, (Perl, D. P., et al. (1980) *Science* 208:297), defects in β-amyloid protein metabolism; (Shoji, M., et al. (192) *Science* 253:126; *Assoc. Disord.* 6:7; Kosik, K. S. (1992) *Science* 256:780; Selkoe, D. J. (1991) *Neuron* 6:487; Hardy, H. and Allsop, D. (1991) *Trends in Pharmacological Science* 12:383; Varghese, J., et al., 1997, *Annual Reports in Medicinal Chemistry* 32:11), and abnormal calcium homeostasis and/or calcium activated kinases. (Mattson, M. P., et al. (1992) *Journal of Neuroscience* 12:376; Borden, L. A., et al. (1991) *Neurobiology of Aging* 13:33; Peterson, E., et al. (1989) *Annals of New York Academy of Science* 568:262; Peterson, C., et al. (1988) *Neurobiology of Aging* 9:261; Peterson, C., et al. (1986) *Proceedings of the National Academy of Science* 83:7999).

Tacrine hydrochloride (COGNEX) was the first drug approved for the treatment of Alzheimer's Disease. Tacrine is a complex pharmacological agent (Cacabelos, R., et al., *Drugs of Today* 1994, 30, 295) which among other properties is a potent inhibitor of acetylcholinesterase (AcChE), and an even more potent inhibitor of the butyrylcholinesterase family of enzymes (Maayani, S., et al., *Biochem. Pharmacol.* 1974, 23, 1263–1281). Tacrine is generally considered to be a postsynaptic agent (Hershenson, F. M. in *New Leads and Targets in Drug Research*, Alfred Benzon Symposium 33, pages 354–363, ed. P. Krogsgaard-Larsen, S. Brogger, H. Kofod; Munksgaard, Copengagen, 1992). Other synaptic AcChE inhibitors include the tacrine analogs, physostigmine (*Drugs of the Future* 1991, 16, 33; ibid. 1994, 19, 343, 656) and physostigmine derivatives, E-2020 (*Drugs of the Future* 1991, 16, 33; ibid. 1994, 19, 343, 656), and huperzine A (*Drugs of the Future* 1991, 16, 33; ibid. 1994, 19, 343, 656).

Tacrine belongs to the well-known structural class of aminopyridines (Osterrieder, W. Br. *J. Pharmac.* 1987, 92, 521; Edwards, G. and Weston, E. H. in *Receptor Data for Biological Experiments, p.* 194, Ellis Horwood, N.Y., 1991) which are potassium channel blockers. The deficiency of tacrine as a drug is related to its liver toxicity and peripheral cholinomimetic actions (Manning, F. C. American *Family Physician* 1994, 50, 819).

Many analogs of tacrine have been prepared (*Drugs of the Future* 1991, 16, 33; ibid. 1994, 19, 343, 656; McKenna, M., et al., *J. Med. Chem.* 1997, 40, 351–3523). Because the 4-aminoquinoline portion of tacrine is generally believed to be important for binding of the drug to the active site of AcChE (Silman, I., et al., *Biochem. Soc. Trans.*, 1994, 22, 745–749), most of these are structurally related to the parent compound, and tend to exhibit some of the same toxicological problems as tacrine. Consequently, there remains a great need for alternative drugs, less structurally related to tacrine, for the treatment of memory impairment such as is associated with Alzheimer's disease.

The systematic name for the benzo[b]quinolizidine ring system is 1,3,4,6,11,11a-hexahydro-2H-benzo[b] quinolizine. Although the parent ring system has been known for some time, derivatives with an amino group at C-11 were not previously known.

With respect to 11-oxygenated derivatives, the C-11 ketone (1,3,4,11a-tetrahydro-2H-benzo[b]quinolizin-11 (6H)-one) is known (G. Gonzalez Trigo and J. Alvarez-Builla, *An. Quim., Ser. C*, 1980, 76: 12–15), as is the 8,9-dimethoxy derivative (Sugimoto, Yakugaku Zasshi (*J. Pharm. Soc. Japan*), 1956, 76, 1045; *Chem. Abstr.* 1957, 3598). The 11-hydroxy derivative (1,3,4,6,11,11a-hexahydro-2H-benzo[b]quinolizin-11-ol) is known (G. Gonzalez Trigo and J. Alvarez-Builla, loc. cit.), as are some 11-aryl and 11-aminoalkyl derivatives (G. E. Hardtnann, U.S. Pat. No. 3,408,352; W. Houlihan and J. Nadelson, U.S. Pat. 3,824,244 and 3,892,752) and the 8,9-dimethoxy derivative (S. Kupchan et al., *J. Org. Chem.*, 1966, 31:1713–1716).

The systematic name for the benzo[f]indolizidine ring system is 1,2,3,5,10,10a-hexahydropyrrolo[1,2-b] isoquinoline. Although the parent ring system has been known for some time, derivatives with an amino group at C-10 have not been reported previously.

With respect to 11-oxygenated derivatives, 1,2,3,5,10, 10a-hexahydropyrrolo[1,2-b]isoquinolin-10-ol is known (Totleben, M. J., et al., *J. Org. Chem.*, 1997, 62:7319–7323; Rigo, B.; Kolocouris, N. *J. Heterocyclic. Chem.* 1983, 20:893–898), as is the 7,8-dimethoxy derivative, and the 10-O-acetate ester thereof (Knefeli, F., et al., *Arch. Pharm.*, 1983, 316:773–781).

A few 3-keto derivatives of the 10-hydroxy compound are also known (Rigo, B., and Kolocouris, N., loc. cit.,; Kubo, A., et al., *Heterocycles*, 1966, 42:195–211).

SUMMARY OF THE INVENTION

In general this invention relates to benzoquinolizidines, benzoindolizidines, and ring-expanded derivatives thereof, and to pharmacological compositions containing these compounds. The compounds of the present invention are benzoquinolizidines, benzoindolizidines, and ring-expanded derivatives of the general formula:

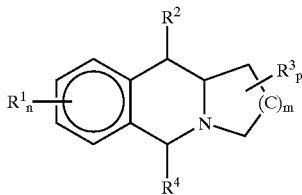

(I)

wherein m, n, p, $R^1$, $R^3$, $R^4$, $R^6$ and $R^7$ are as defined further below.

The compounds of this invention are expected to be useful for enhancing cognition, and for treating or controlling the symptoms of memory impairment in senile dementia, Alzheimer's disease, or similar conditions. Although some of these conditions may be associated with decreased availability of acetylcholine, and although the compounds of this invention are in general weak inhibitors of acetylcholinesterase, the present invention is not limited with regard to any specific mechanism of action, nor are the memory-enhancing properties of the compounds of the invention attributed to any specific mechanism.

DETAILED DESCRIPTION OF THE INVENTION

The present invention provides benzoquinolizidines, benzoindolizidines, and ring-expanded derivatives thereof, wherein a tetrahydroisoquinoline is fused to a pyrrolidine, piperidine, azepine or azocine ring. These compounds are of the general formula:

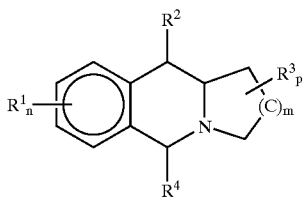

(I)

wherein n=1 to 4, and each $R^1$ independently may be hydrogen, halo, or optionally substituted alkyl or cycloalkyl, aryl, arylalkyl, haloalkyl, haloalkoxy, hydroxy, alkoxy, trifluoromethyl, cyano, carboalkoxy, alkanoyl, aroyl, or alkylsulfonyl;

wherein $R^2$=$OR^5$ or $NR^6R^7$, and $R^5$ is hydrogen, optionally substituted alkyl or cycloalkyl, alkanoyl, aroyl, aryl, arylalkyl, alkylaryl, haloalkyl, or haloalkoxy, and $R^6$ and $R^7$ may each independently be hydrogen, optionally substituted alkyl or cycloalkyl, aryl, arylalllyl, alkylaryl, aroyl, alkanoyl, alkylaroyl, or arylalkanoyl, or $NR^6R^7$ may be azetidino, pyrrolidino, piperidino, or morpholino;

wherein p=1 to 6, and $R^3$ is hydrogen, hydroxy, alkoxy, halo, optionally substituted alkyl or cycloalkyl, aryl, arylalkyl, alkylaryl, haloallyl, haloalkoxy;

wherein $R^4$ is hydrogen, optionally substituted alkyl or cycloalkyl, aryl, arylalkyl, alkylaryl, haloalkyl, or haloalkoxy; and wherein m=1 to 4.

Halo includes bromo, iodo, fluoro or chloro; preferably chloro, bromo or fluoro; and most preferably is chloro or fluoro.

The term "alkyl", alone or in combination, is intended to include straight chain and branched alkyl groups containing from 1 to about 10 carbons, preferably from 1 to about 8 carbon atoms. Examples include, but are not limited to, methyl, ethyl, n-propyl, isopropyl, n-butyl, isobutyl, sec-butyl, tert-butyl, amyl, isoamyl, hexyl, octyl and the like.

The term "cycloalkyl", alone or in combination, is intended to include a saturated or partially saturated monocyclic alkyl radical which contains from 3 to about 8 carbon atoms. Examples of such cycloalkyl radicals include cyclopropyl, cyclobutyl, cyclopentyl, cyclohexyl, 3-cyclohexenyl, cycloheptyl, cyclooctyl, and the like.

The term "aryl", used alone or in combination, is intended to include an aromatic hydrocarbon which may be monocyclic, bicyclic, or tricyclic, such as phenyl, naphthyl, or anthryl, which optionally carries one or more substituents selected from alkyl, alkanoyl, alkoxy, halogen, hydroxy, amino, nitro, cyano, alkylsulfonyl, haloalkyl and the like. Examples include p-tolyl, 4-ethoxyphenyl, 4-(t-butoxy) phenyl, 4fluorophenyl, chlorophenyl, 4-acetylphenyl, 4-hydroxyphenyl, 1-naphthyl, 2-naphthyl, and the like.

The term "arylalkyl", alone or in combination, is an alkyl as defined above in which one hydrogen atom is replaced by an aryl radical as defined above, such as for example benzyl, 2-phenylethyl, and the like.

The term "haloalkyl" is intended to include an alkyl radical having the significance as defined above wherein one or more hydrogens are replaced with a halogen. Examples of such haloalkyl radicals include, but are not limited to, chloromethyl, 2-bromoethyl, fluoromethyl, difluoromethyl, trifluoromethyl, 2,2,2-trifluoroethyl and the like.

The terms "cis" and "trans" refer to the stereochemical relationship between the benzylic substituent (in the benzo [b]quinolizidines, on C-11) and the bridgehead hydrogen (in the benzo[b]quinolizidines, on C-11a). The corresponding positions in the benzo[f]indolizidines are at C-10 and C-10a. The sterochemistry of the compounds may be readily determined from the $^1$H NMR spectra. The trans isomers are characterized by a coupling constant of 1 to 3 Hz between the H-11 and H-11a, whereas the cis isomers are characterized by a coupling constant of 8 to 11 Hz.

Examples of optional substituents include, but are not limited to, alkyl, cycloalkyl, aryl, arylalkyl, alkylaryl, heteroaryl, alkoxy, halogen, hydroxy, amino, nitro, cyano, alkylsulfonyl, haloalkyl, and the like. The optional substituents may themselves be optionally substituted, for example $R^1$ may be 3-chlorobenzyloxy or the like.

Heteroaryl refers to an aromatic group of from 1 to 9 carbon atoms and 1 to 4 heteroatoms selected from oxygen, nitrogen and sulfur within the ring. Such heteroaryl groups can have a single ring (e.g., pyridyl, tetrazolyl, or furyl) or multiple condensed rings (e.g., indolyl, quinolyl, or benzothienyl), which can optionally be unsubstituted or substituted with hydroxy, alkyl, alkoxy, halo, mercapto, and the like. Preferred heteroaryls include for example pyridyl and furyl.

The term alkanoyl refers to an alkyl group as defined above, attached to a carbonyl group, and the term aroyl refers to an aryl group as defined above, attached to a carbonyl group.

Throughout the specification and the appended claims, a given chemical formula or name shall encompass all stereo and optical isomers thereof where such isomers exist, as well as pharmaceutically acceptable acid addition salts thereof and solvates thereof such as, for instance, hydrates. Separate enantiomeric forms or racemic mixtures of the compounds are also within the scope of this invention.

Preferred compounds of the invention conform to the following formulae:

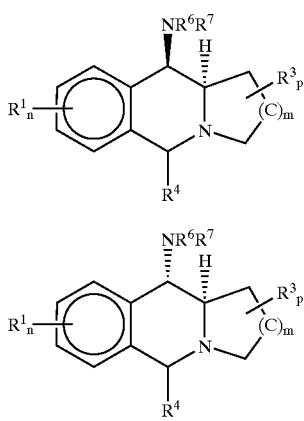

wherein $R^1$ through $R^7$, m, n and p are as described above. More preferably, m is 1 or 2. Preferred compounds include the following:

- $R^1$ is H, $R^3$ is H, $R^4$ is H, $R^6$ is H, $R^7$ is H and m is 2 (trans-1,3,4,6,11,11a-hexahydro-11-amino-2H-benzo[b]quinolizine);
- $R^1$ is H, $R^3$ is H, $R^4$ is H, $R^6$ is H, $R^7$ is methyl, and m is 2 (trans-1,3,4,6,11,11a-hexahydro-11-methylamino-2H-benzo[b]quinolizine);
- $R^1$ is H, $R^3$ is H, $R^4$ is H, $R^6$ is H, $R^7$ is benzyl, and m is 2 (trans-1,3,4,6,11,11a-hexhydro-11-benzylamino-2H-benzo[b]quinolizine);
- $R^1$ is 9-methoxy, $R^3$ is H, $R^4$ is H, $R^6$ is H, $R^7$ is methyl, and m is 2 (trans-9-methoxy-1,3,4,6,11,11a-hexahydro-11-methylamino-2H-benzo[b]quinolizine);
- $R^1$ is 9-methoxy, $R^3$ is H, $R^4$ is H, $R^6$ is H, $R^7$ is benzyl and m is 2 (trans-9-methoxy-1,3,4,6,11,11a-hexahydro-11-benzylamino-2H-benzo[b]quinolizine);
- $R^1$ is 8-chloro, $R^3$ is H, $R^4$ is H, $R^6$ is H, $R^7$ is methyl and m is 2 (trans-8-chloro-1,3,4,6,11,11a-hexahydro-11-methylamino-2H-benzo[b]quinolizine);
- $R^1$ is H, $R^3$ is H, $R^4$ is H, $R^6$ is H, $R^7$ is methyl, and m is 1 (cis-1,2,3,5,10,10a-hexahydro-10-(methylamino)-pyrrolo[1,2-b]isoquinoline);
- $R^1$ is H, $R^3$ is H, $R^4$ is H, $R^6$ is H, $R^7$ is alkanoyl and m is 2 (trans-1,3,4,5,11,11a-hexahydro-11-alkanoylamino-2H-benzo[b]quinolizine); and
- $R^1$ is H, $R^3$ is H, $R^4$ is H, $R^6$ is H, $R^7$ is n-butyryl and m is 2 (trans-1,3,4,5,11,11a-hexahydro-11-butyrylamino-2H-benzo[b]quinolizine).

Preferably, when m is 2, the compounds are in the trans configuration, as shown in Formula 2.

Other compounds of the invention conform to the following formulae:

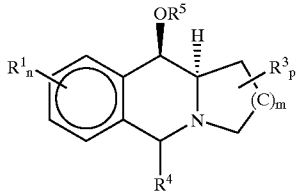

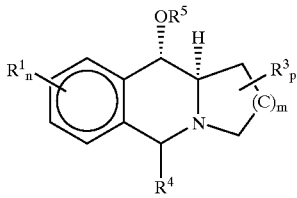

wherein $R^1$ through $R^5$, m, n and p are as described above.

In a preferred embodiment, $R^1$ is H and n is 1, $R^3$ is H and p is 4, $R^4$ is H, $R^5$ is alkanoyl, such as acetyl or propionyl, and m=2.

When m is 2, the compound is preferably in the trans configuration as in formula 4.

The compounds of formula 1 can be prepared by the following methods. Compounds of the formula 6 can be converted to compounds of general formula 1 via an imine intermediate 7 or via an alcohol intermediate 8.

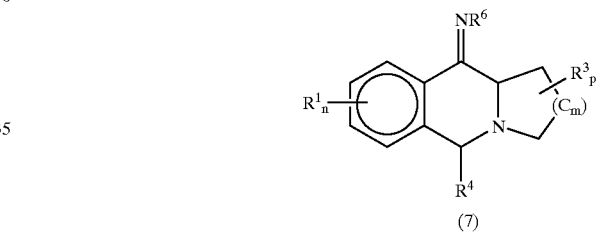

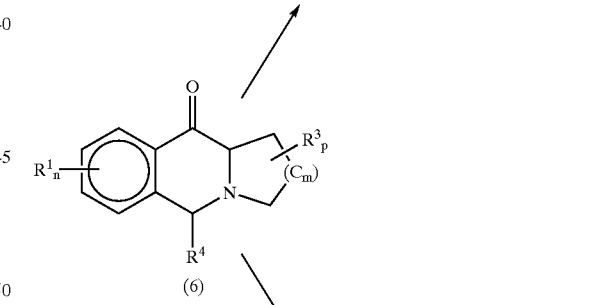

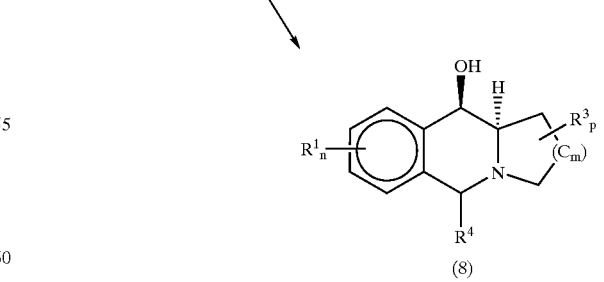

The starting ketone 6 can be prepared according to the literature (Gonzalez Trigo, G.; Alvarez-Builla, J. *An. Quim., Ser. C* 1980, 76, 12). Accordingly, an ethyl pipecolinate hydrochloride 9 can be allowed to react with a substituted benzyl chloride in the presence of a base, for example, potassium carbonate ($K_2CO_3$), sodium carbonate ($Na_2CO_3$), or lithium carbonate, ($Li_2CO_3$). The resulting ester 11 can be hydrolyzed, for example with concentrated hydrochloric acid, to an acid 12 which can be cyclized under Friedel-Craft conditions, for example with aluminum chloride. polyphosphoric acid (PPA), or phosphorous pentoxide in methanesulfonic acid (Eaton's reagent), to give the ketone 6.

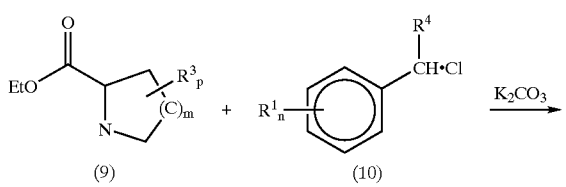

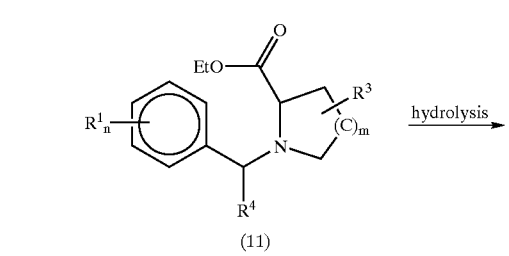

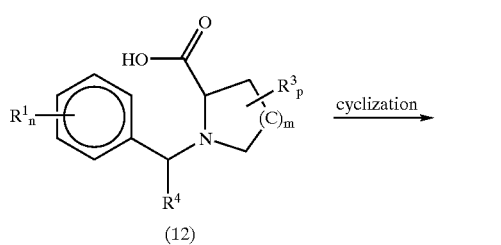

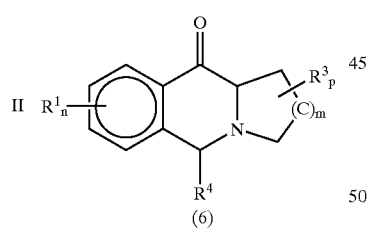

The reductive amination of ketone 6 can be accomplished by reaction of the ketone 6 with an amine in an organic solvent, preferably in the presence of a catalyst and dehydrating agent, such as for example titanium tetrachloride ($TiCl_4$). The solvent can then be removed by conventional methods, including but not limited to evaporation in vacuo. After the reaction of the ketone with the amine, the resultant imine 7 is reduced with a reducing agent such as, for example, sodium cyanoborohydride, lithium aluminum hydride (LAH), or by catalytic hydrogenation, to give the desired amine as the trans isomer 2.

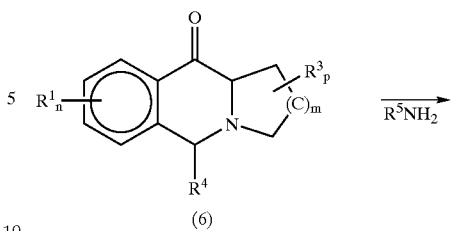

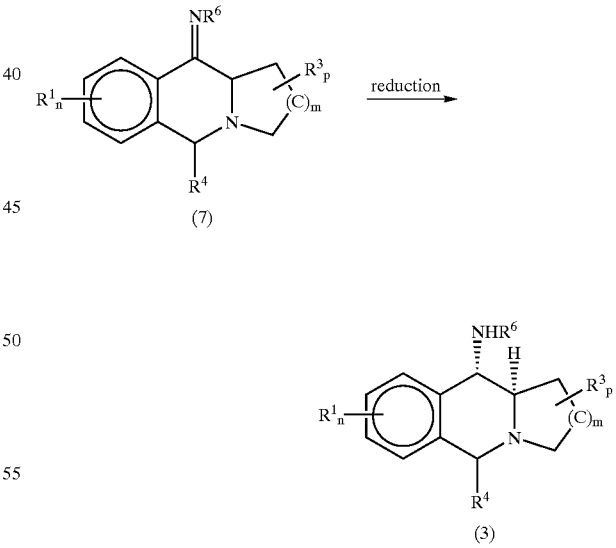

The cis isomer 3 can be obtained by a dissolving metal reduction of imine 7, for example by reduction with sodium metal in ethanol. Reaction with sodium in ethanol appears generally to favor the thermodynamically more stable product 3 as the major isomer (Rausser, R.; Weber, L.; Hershberg, E. B.; Oliveto, E. P. *J. Org. Chem.* 1966, 31, 1342–1346).

The trans N-benzyl derivatives (2, $R^6$=benzyl) can be prepared via an N-benzyl imine (for example 7, $R^6$=benzyl) by hydrogenation under neutral conditions.

When the benzylamino derivative is subjected to further hydrogenation in the presence of an acid, as for example hydrochloric acid, the benzyl group is cleaved to give a trans primary amine (2, $R^6$=H).

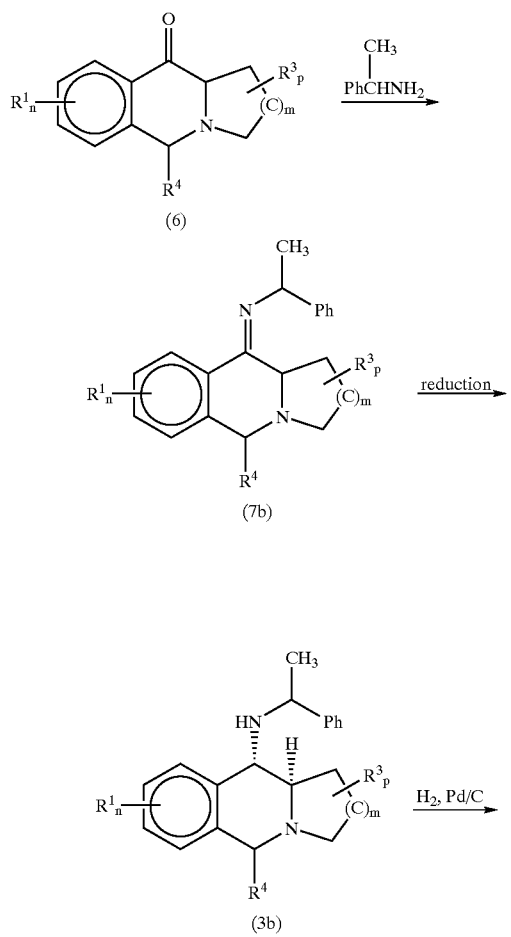

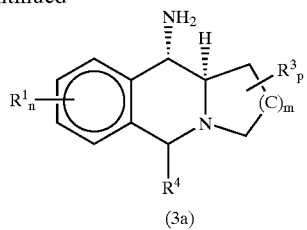

The cis isomer, when $R^6$ and $R^7$ are both H (3, $R^6$=H), can be obtained from the α-(methyl)benzylimine intermediate 7b (Bolton, R.; Danks, T. N.; Paul, J. M. *Tetrahedron Lett.* 1994, 35, 3411) which can be reduced, for example with sodium borohydride, to secondary amine 3b and then hydrogenolyzed, for example with palladium on carbon, to give a primary cis amine 3a.

A single enantiomer of α-(methyl)benzylamine may be employed, and separation of the diasteromers of 3b, for example by chromatography, may be carried out, so as to obtain a single enantiomer of 3a upon hydrogenolysis. A similar procedure will provide the trans enantiomers (2, $R^6$=H).

Ketone 6 may also be hydrogenated, for example with palladium on carbon in tetrahydrofuran and hydrochloric acid, to provide the cis and trans alcohols 12 and 8, which may then be converted to the corresponding esters, for example the acetates 13 and 14, by treatment with an acyl chloride or anhydride in the presence of a base such as pyridine, 4-(dimethylamino)pyridine, and/or triethylamine.

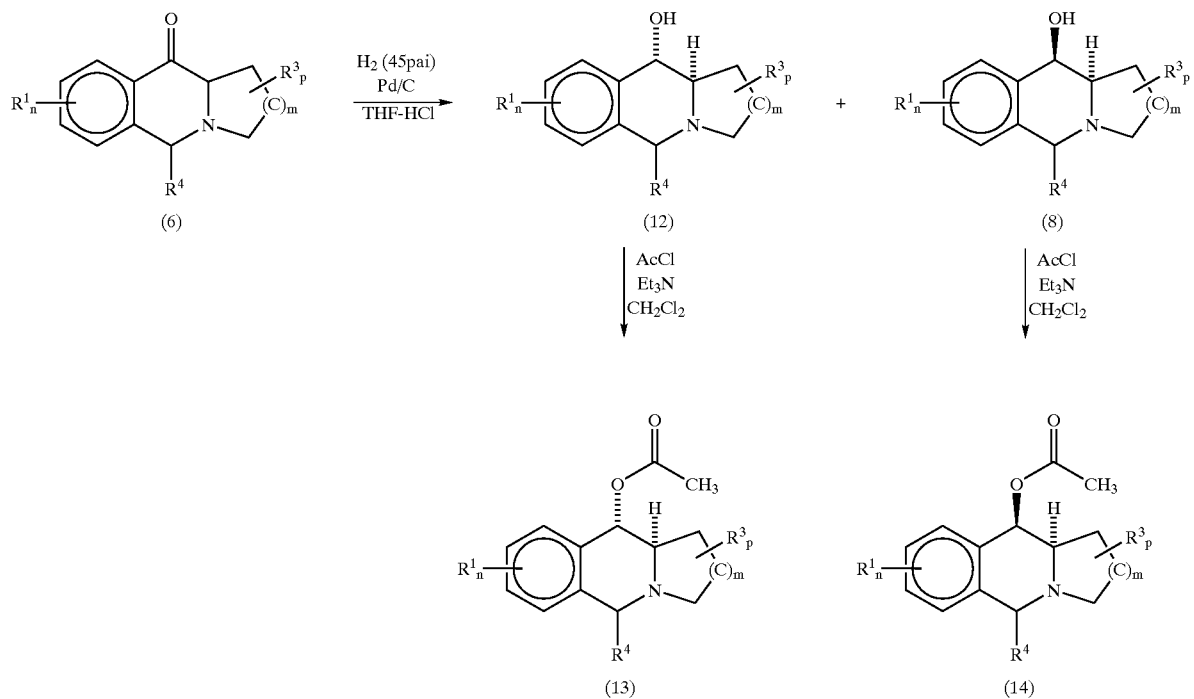

Amide derivatives of structure 16 can also be synthesized by the acylation of 15 with an acyl chloride or anhydride in the presence of a base such as pyridine, 4-(dimethylamino)pyridine, and/or triethylamine.

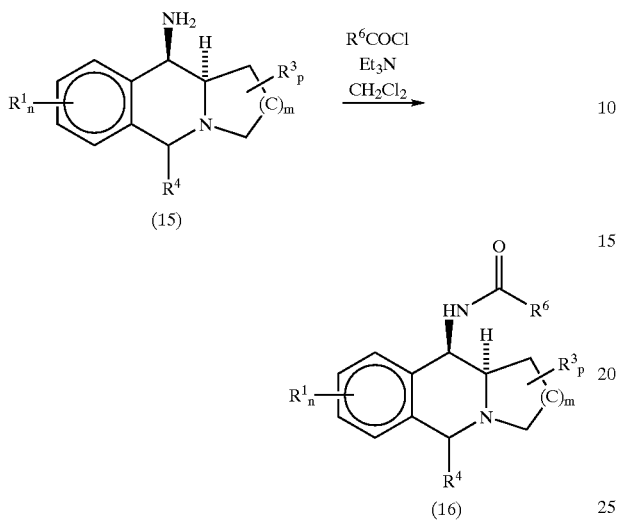

A particular amide which may be synthesized is derived from 2-oxo-1-pyrrolidineacetic acid 18. The reaction of 18 and 2a in the presence of carbonyl diimidazole (CDI) gives the amide 19.

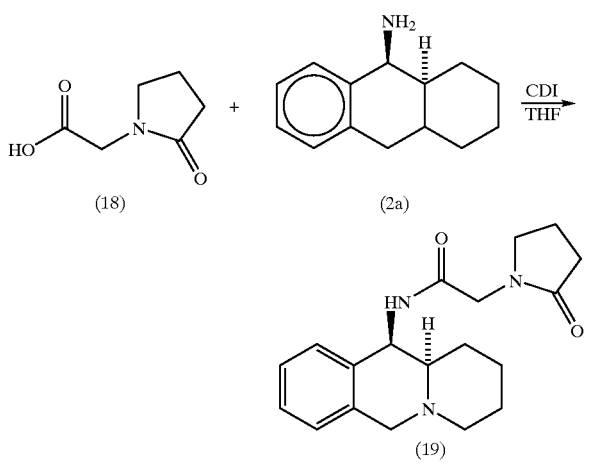

An alternative method for synthesizing compounds of the formula 2 is as follows. Pyrrolidinonecarboxylic acid 21 can be converted to a ketone 22 (Rigo, B.; Kolocouris, N. *J. Heterocyclic. Chem.* 1983, 20, 893). The ketone can then be converted to imine 23, and the imine can be hydrogenated to give trans amino-ketone 24, with the amide carbonyl intact. Alternatively, borohydride reduction of 23 provides the corresponding cis amino-ketone. Reduction of 23 or 24, for example by lithium aluminum hydride or borane, is also expected to reduce the amide carbonyl of 24 to provide compounds of structure 2 (see the preparation of 32 below).

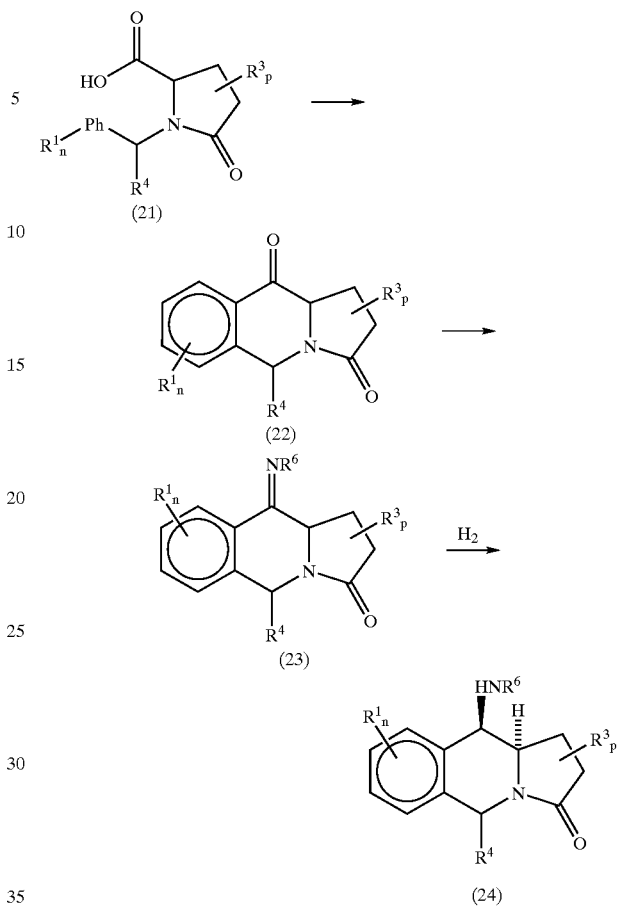

The pyrrolidinonecarboxylic acid 21 can be synthesized by a multi-step procedure described in the literature (Buckley III, T. F.; Rapoport, H. *J. Org. Chem.* 1984, 48, 4222), with modifications. Thus; an optionally subsituted d,l-glutamic acid 26 is esterified, for example with isopropanol in the presence of sulfuric acid. The resulting ester 27 is benzylated on nitrogen by reaction with an arylmethyl halide, such as benzyl chloride, in the presence of a base such as potassium carbonate. Cyclization of the resulting compound 28 can be carried out by mild heating under acidic conditions, for example in methanol and acetic acid, to give a pyrrolidinone ester 29. The acid 21 is obtained by the saponification of ester 29.

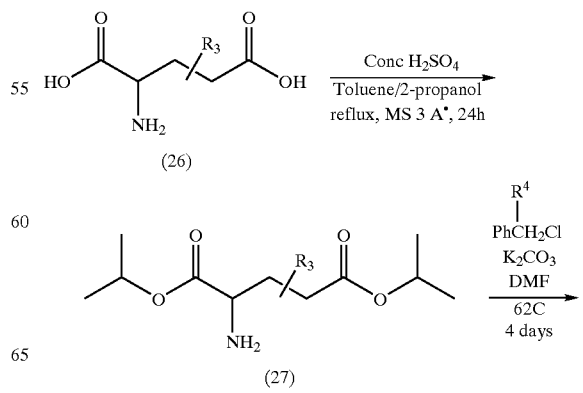

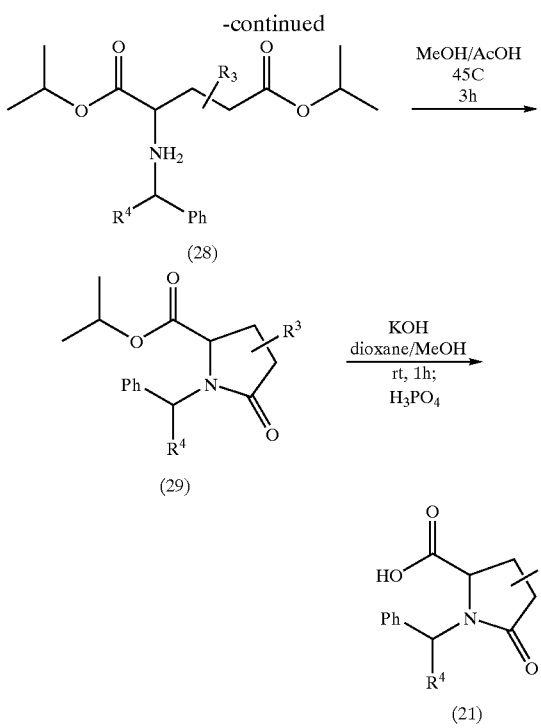

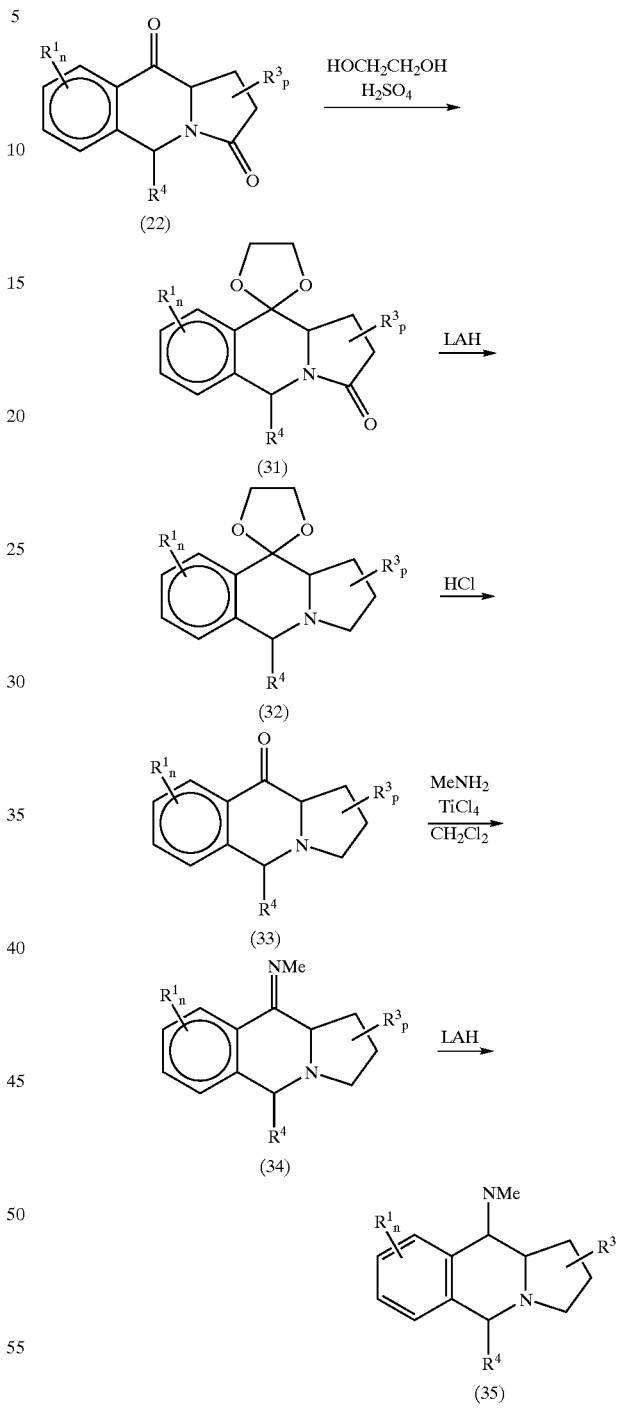

Heterocyclic. Chem. 1983, 20, 893), ketone 22 was first protected as ketal 31 which was then subjected to LAH reduction.

Alternatively, acid 21 can be prepared from d,l-glutamic acid by modification of a two step procedure described in the literature (Ohfune, Y.; Kurokawa, N.; Higuchi, N.; Saito, M.; Hashimoto, M.; Tanaka, T. Chem Let. 1984, 441; and Peterson, J. S.; Fels, G.; Rapoport, H. J. Am. Chem. Soc. 1984, 106, 4539). Specifically, the reductive amination of d,l-glutamic acid with $NaBH_3CN$ in the presence of benzaldehyde gave N-benzylated glutamic acid 20 ($R^4$=H). Acid 21 ($R^4$=H) was obtained by heating 20 in water.

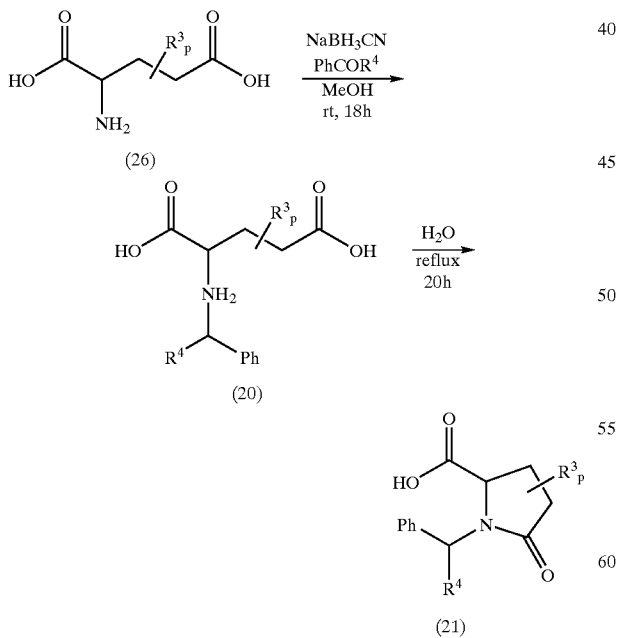

An alternative strategy to prepare compounds of structure 6 (m=1) involves the initial reduction of the amide carbonyl of compound 22. As reported (Rigo, B.; Kolocouris, N. J.

The resulting ketal 32 was deprotected under acidic conditions to give ketone 33 (Rigo, B.; Kolocouris, N., J. Heterocyclic. Chem. 1983, 20, 893). Compound 33 can then be converted, by the methods described herein, to imine 34 and then to amine derivative 35.

Yet another method for synthesizing ketone 33 is by reduction of the ketone 22 to alcohol 36 (Rigo, B.; Kolocouris, N. J. Heterocyclic. Chem. 1983, 20, 893) which can then be oxidized to ketone 37 (Szmuszkovicz, J.; Skaletzky, L. L. *J. Org. Chem.* 1967, 32, 3300).

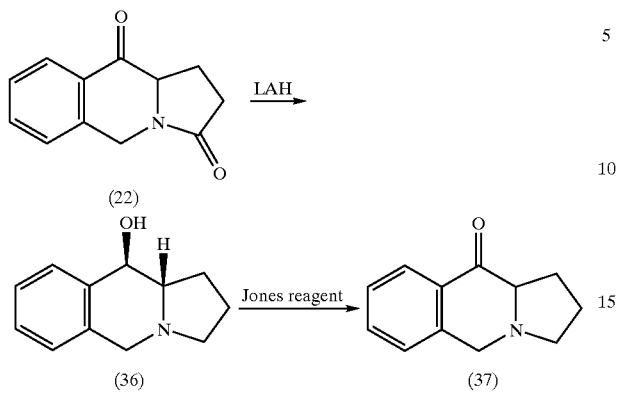

This invention also provides methods of treating or controlling disease states characterized by the symptom of memory loss, such as Alzheimer's disease, senile dementia, or similar conditions, comprising administering a therapeutically effective amount of at least one of the compounds of the present invention, pharmaceutically-acceptable salts thereof, or mixtures thereof.

Compounds to be administered may have the general formula:

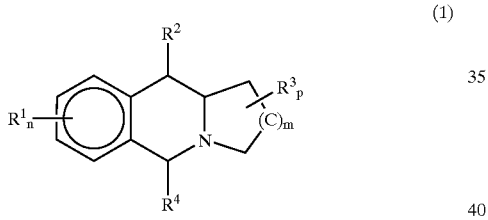

wherein n=1 to 4, and each $R^1$ independently may be hydrogen, halo, or optionally substituted alkyl, cycloalkyl, aryl, arylalkyl, haloalkyl, haloalkoxy, hydroxy, alkoxy, trifluoromethyl, cyano, carboalkoxy, alkanoyl; or alkylsulfonyl;

wherein $R^2=OR^5$ or $NR^6R^7$, and $R^5$ is a hydrogen or optionally substituted alkyl, cycloalkyl, alkanoyl, aryl, arylalkyl, arylakyl, haloalkyl, or haloalkoxy; and $R^6$ and $R^7$ may each independently be hydrogen or optionally substituted alkyl, cycloalkyl, aryl, arylalkyl or alkylaryl or optionally substituted alkyl carbonyl, alkylaryl carbonyl, or $NR^6R^7$ may be azetidino, pyrolidino, piperidino, or morpholino;

wherein p=1 to 6, and $R^3$ is hydrogen, hydroxy, alkoxy, halo, optionally substituted alkyl or cycloalkyl, aryl, arylalkyl, alkylaryl, haloalkyl, haloalkoxy;

wherein $R^4$ is hydrogen, optionally substituted alkyl or cycloalkyl, aryl, arylalkyl, alkylaryl, haloalkyl, or haloalkoxy; and wherein m=1 to 4.

In certain preferred embodiments of the invention, the compounds to be administered conform to the following formulae:

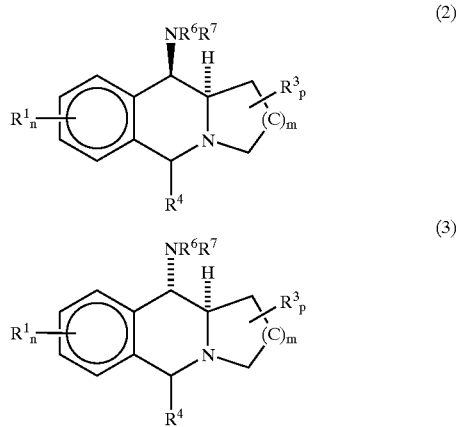

wherein $R^1$ is H, $R^3$ is H, $R^4$ is H, $R^6$ is H, $R^7$ is H and m is 2 (trans-1,3,4,6,11,11a-hexahydro-11-amino-2H-benzo[b]quinolizine);

$R^1$ is H, $R^3$ is H, $R^4$ is H, $R^6$ is H, $R^7$ is methyl, and m is 2 (trans-1,3,4,6,11,11a-hexahydro-11-methylamino-2H-benzo[b]quinolizine);

$R^1$ is H, $R^3$ is H, $R^4$ is H, $R^6$ is H, $R^7$ is benzyl, and m is 2 (trans-1,3,4,6,11,11a-hexhydro-11-benzylamino-2H-benzo[b]quinolizine);

$R^1$ is 9-methoxy, $R^3$ is H, $R^4$ is H, $R^6$ is H, $R^7$ is methyl, and m is 2 (trans-9-methoxy-1,3,4,6,11,11a-hexahydro-11-methylamino-2H-benzo[b]quinolizine);

$R^1$ is 9-methoxy, $R^3$ is H, $R_4$ is H, $R^6$ is H, $R_7$ is benzyl and m is 2 (trans-9-methoxy-1,3,4,6,11,11a-hexahydro-11-benzylamino-2H-benzo[b]quinolizine);

$R^1$ is 8-chloro, $R^3$ is H, $R^4$ is H, $R^6$ is H, $R^7$ is methyl and m is 2 (trans-8-chloro-1,3,4,6,11,11a-hexahydro-11-methylamino-2H-benzo[b]quinolizine);

$R^1$ is H, $R^3$ is H, $R^4$ is H, $R^6$ is H, $R^7$ is methyl, and m is 1 (cis-1,2,3,5,10,10a-hexahydro-10-(methylamino)-pyrrolo[1,2-b]isoquinoline);

$R^1$ is H, $R^3$ is H, $R^4$ is H, $R^6$ is H, $R^7$ is alkanoyl and m is 2 (trans-1,3,4,5,11,11a-hexahydro-11-alkanoylamino-2H-benzo[b]quinolizine); and $R^1$ is H, $R^3$ is H, $R^4$ is H, $R^6$ is H, $R^7$ is n-butyryl and m is 2 (trans-1,3,4,5,11,11a-hexahydro-11-butyrylamino-2H-benzo[b]quinolizine).

Preferably, when m is 2, the compounds are in the trans configuration, as shown in Formula 2.

In other preferred embodiments of the invention, the compounds to be administered conform to the following formulae:

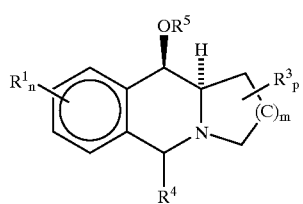

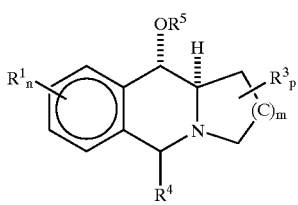

(5)

wherein
R¹ is H, R³ is H, R⁴ is H, R⁵ is H, and m is 2 (trans-1,3,4,6,11,11a-hexahydro-2H-benzo[b]quinolizidin-11-ol),
R¹ is H, R³ is H, R⁴ is H, R⁵ is alkanoyl, and m is 2 (O-alkanoyl-trans-1,3,4,6,11,11a-hexahydro-2H-benzo[b]quinolizidin-11-ol).

More preferably, R⁵ is acetyl, and preferably the compounds are in the trans configuration as shown in formula 4.

The activity associated with the compounds of this invention may be determined based on an in vitro assay or an in vivo assay. By way of example, an in vitro technique that may be used includes, but is not limited to, assessment of inhibition of acetylcholinesterase activity in the presence of the compounds of this invention. Accordingly, acetylcholinesterase activity is assessed in the presence of varying concentrations of the compound of the invention. The preferred compounds are capable of inhibiting acetylcholinesterase activity in vitro.

Alternatively, the activity associated with the compounds of this invention may be assessed by an in vivo assay such as the reversal or antagonism of scopolamine-impaired passive avoidance learning. Preferred compounds are capable of reversing the impairment of learning induced by administered scopolamine.

An effective amount of the compounds of this invention is a dosage sufficient to control or alleviate the symptoms of the disease state or condition of the subject. The dosage of the compounds of this invention will vary depending upon several parameters including, but not limited to, the age of the subject, the severity and type of the disease state, the general health of the subject and other parameters known to one skilled in the art. Based on such parameters the treating physician will determine the therapeutically effective amount of the compound for a given individual. Such therapies may be administered as often as necessary and for the period of time judged necessary by the treating physician. The compounds of the present invention may be administered alone or in combination with other therapies.

Effective quantities of the compounds of the invention may be administered to a patient by any of the various methods, for example, orally as in capsules, tablets, or suspensions; rectally in the form of suppositories; parenterally in the form of sterile solutions or suspensions; and in some cases intravenously in the form of sterile solutions. The free base final products, while effective themselves, may be formulated and administered in the form of their pharmaceutically acceptable acid addition salts for the purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, malic, fumaric, oxalic, medhanesulfonic and toluenesulfonic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations may contain about 5 mg to about 200 mg of the active compound, but may be varied depending upon the particular form. The amount of active compound in such compositions is such that a suitable dosage will be obtained.

The tablets, pills, capsules, troches and the like may also contain the following ingredients: a binder such as microcrystalline cellulose, gum tragacanth or gelatin; an excipient such as starch or lactose, a disintegrating agent such as alginic acid, Promogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purposes of parenteral therapeutic administration, the active compounds of the invention may be incorporated into a solution or suspension. The amount of active compound in such compositions is such that a suitable dosage will be obtained. The compositions and preparations according to the present invention may be prepared so that a parenteral dosage unit contains between about I mg to about 30 mg of active compound.

The solutions or suspension may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

All books, articles and patents referenced herein are incorporated by reference. The following examples illustrate various aspects of the invention but are in no way intended to limit the scope therof.

EXAMPLES

1. Preparation of the Compounds.

Example 1

Ethyl N-(methoxyphenylmethyl)pipecolinate. 4-Methoxy benzyl chloride (55 mmol, 8.61 g) was add ed t o a mixture of K$_2$C$_3$ (56 mmol, 7.7 4 g) and ethyl pipecolinate hydrochloride (50 mmol, 9.68 g) in DMF (55 mL). The mixture was stirred for 3 days at 62° C., and was filtered. Ice-cold HCl solution (1.5 N, 50 mL) was added to the filtrate and it was extracted with ether (3×100 mL). The aqueous phase was basified with NaOH solution (40%) and extracted with ether (5×100 mL). The combined extracts were washed with brine, dried with Na$_2$SO$_4$ and MgSO$_4$ and concentrated in vacuo to give ethyl N-(4-methoxyphenylmethyl)-pipecolinate as a yellow oil (7.12 g): $^1$H NMR (300 MHz) δ 7.23 (d, J=8.6 Hz, 2 H), 6.84 (d, J=8.6 Hz, 2 H), 4.22 (q, J=7.1 Hz, 2 H), 3.70 (s, Me), 3.73 (d, J=13.1 Hz, 1 H), 3.34 (d, J=13.6 Hz, 1 H), 3.08 (dd, J=8.2, 4.3 Hz, 1 H), 2.93 (m, 1 H), 2.10 (m, 2 H), 1.80 (m, 2 H), 1.56 (m, 3 H), 1.30 (t, J=7.1 Hz, 3 H); $^{13}$C NMR δ 174.00, 158.68, 130.43, 130.01, 113.46, 64.55, 60.30, 59.87, 55.20, 50.15, 29.64, 25.24, 22.67, 14.33; MS (E) 277 (2, M), 204 (90), 121 (100); HRMS (EI) m/e calcd for C$_{16}$H$_{23}$NO$_3$ 277.1678, found 277.1682.

Example 2

Ethyl N-(3chlorophenylmethyl)pipecolinate. A mixture of 3thlorobenzyl chloride (11 mmol, 1.4 mL), ethyl pipecolinate hydrochloride (10 mmol, 1.94 g) and K$_2$CO$_3$ (12 mmol, 1.69 g) in DMF (10 mL) was stirred at 60° C. for 3 days. It was then diluted with ether (50 mL) and filtered. The filtrate was concentrated in vacuo to give ethyl N-(3chlorophenylmethyl)pipecolinate as a yellow oil (2.79g): $^1$H NMR (300 MHz) δ 7.21–7.35 (m, 4 H), 4.20 (q, J=7.1 Hz, 2 H), 3.77 (d, J=13.6 Hz, 1 H), 3.37 (d, J=13.6 Hz, 1 H), 3.14 (dd, J=7.5 Hz, 4.6 Hz, 1 H), 2.92 (dt, J=11.9, 5.4 Hz, 1 H), 2.15 (m, 1 H), 1.34–1590 (m, 6 H), 1.29 (t, J=7.1 Hz, 3 H); $^{13}$C NMR δ 173.74 (s), 140.73 (s), 134.06 (s), 129.35 (d), 128.99 (d), 127.14 (d), 64.33 (d), 60.34 (t), 59.98 (t), 50.11 (t), 29.52 (t), 25.25 (t), 22.39 (t), 14.30 (q); MS (FAB) 282 (98, M+H), 208 (100); HRMS (FAB) m/e calcd for (C$_{15}$H$_{20}$ClNO$_2$+H) 282.1261, found 282.1248.

Example 3

N-(4Methoxyphenylmethyl)pipecolinic acid hydrochloride. A mixture of the compound of Example 1 (7.12 g) and conc. HCl (100 mL) was refluxed for 8 h. Solvent was removed in vacuo and 2-propanol was added to the residue. Upon cooling, a pale yellow solid was obtained as N-(4-methoxyphenylmethyl)pipecolinic acid hydrochloride (2.08 g): mp 199–201° C. (2-propanol); $^1$H NMR (300 MHz, D$_2$O) δ 7.42 (d, J=8.1 Hz, 2 H), 7.05 (d, J=8.1 Hz, 2 H), 4.45 (d, J=13.1 Hz, 1 H), 4.09 (d, J 13.1 Hz, 1 H), 3.84 (s, Me); MS (EI) 249 (2, M), 204 (38), 121 (100); Anal. Calcd for C$_{14}$H$_{19}$NO$_3$.HCl.0.2H$_2$O: C, 58.11; H, 7.11; N 4.84; Cl, 12.25; found C, 58.02; H, 7.21; N, 4.64; Cl, 12.57. The mother liquor was concentrated to give a foam (5.59 g) which was identical to N-(4methoxyphenylmethyl)-pipecolinic acid hydrochloride by $^1$H NMR.

Example 4

N-(3-Chlorophenyhnethyl)pipecolinic Acid Hydrochloride. Using the same procedure as above, ethyl N-(3-chlorophenylmethyl)pipecolinate (see example 2, 2.79 g) was converted to N-(3-chlorophenylmethyl)pipecolinic acid hydrochloride (2.78 g): mp 221–223° C. (MeOH/2-propanol); $^1$H NMR (300 MHz, D$_2$O) δ 7.40–7.55 (m, 4 H), 4.54 (d, J=12.9 Hz, 1 H), 4.13 (d, J=13.2 Hz, 1 H), 3.88 (dd, J=11.9 Hz, 3.5 Hz, 1 H), 3.48 (br d, J=12.9 Hz, 1 H), 3.02 (td, J=12.6, 3.0 Hz, 1 H), 2.31 (m, 1 H), 1.50–1.90 (m, 5 H); 13C NMR (75 MHz, D$_2$O) δ 172.08, 134.25, 131.24, 130.67, 130.31, 130.25, 129.87, 65.37, 59.12, 51.66, 27.80, 21.95, 20.77; MS (FAB) 253 (2, M), 208 (100), 125 (59); Anal. Calcd for C$_{13}$H$_{16}$ClNO$_2$.HCl: C, 53.81; H, 5.90; N 4.83; Cl, 24.43; found C, 53.52; H, 6.14; N, 4.85; Cl, 24.15.

Example 5

1,3,4,11a-Tetrahydro-2H-benzo[b]quinolizin-11(6H)-one. The following is a modification of the procedure reported (Gonzalez Trigo, G.; Alvarez-Builla, *J. An. Quim., Ser. C* 1980, 76, 12). N-benzylpipecolinic acid (5.10 g, 20.0 mmol) was placed in a 500 mL flask. Polyphosphoric acid (200 g) was added. The mixture was heated in an oil bath gradually to 140° C. with stirring. It was stirred at 140° C. until the bubbling stopped, then cooled to room temperature and poured into ice. The mixture was neutralized with aqueous NaGH (40%) and extracted with ether (5×80 mL). The combined extracts were washed with brine, dried (Na$_2$SO$_4$) and concentrated in vacuo to give a red solid (3.08 g, 77%): m.p. 71–72° C. (benzene); $^1$H NMR (300 MHz) δ 8.02 (dd, J=7.8, 1.3 Hz, 1 H), 7.50 (td, J=7.3, 1.4 Hz, 1 H), 7.35 (t, J=7.6 Hz, 1 H), 7.23 (d, J=7.6 Hz, 1 H), 3.88 (d, J=15.2 Hz, H-6), 3.68 (d, J=14.9 Hz, H-6), 3.09 (br d, J=11.2 Hz, 1 H), 2.77 (br d, J=10.5 Hz, 1 H), 2.44 (m, 1 H), 2.35 (td, J=11.3, 3.5 Hz, 1 H), 1.90 (br d,J=12.5 Hz, 1 H), 1.32–1.76 (m, 4 H); $^{13}$C NMR (75 MHz) δ 195.87, 141.73, 133.53, 130.12, 127.34, 127.00, 126.17, 69.21, 57.14, 56.13, 26.66, 25.02, 23.81.

Example 6

1,3,4,11a-Tetrahydro-9-methoxy-2H-benzo[b]quinolizin-11(6H)-one. By the above procedure, N-(4-methoxyphenylmethyl)pipecolinic acid hydrochloride (2.98 g) was converted to 1,3,4,11a-tetrahydro-9-methoxy-2H-benzo[b]quinolizin-11(6R)-one (950 mg): mp 117–119° C. (ether); $^1$H NMR (300 MHz) δ 7.48 (d, J=2.7 Hz, 1 H), 7.14 (d, J=8.4 Hz, 1 H), 7.08 (dd, J=8.4, 2.7 Hz, 1 H), 3.84 (s, Me), 3.84(d, J=14.8 Hz, 1 H), 3.61 (d, J=14.8 Hz, 1 H), 3.08 (br d, J=11.1 Hz, 1 H), 2.74 (br d, J=10.1 Hz, 1 H), 2.42 (m 1 H), 2.34 (td, J=11.3, 3.6 Hz, 1 H), 1.90 (m, 1 H), 1.15–1.80 (m); $^{13}$C NMR (75 MHz) δ 195.89, 158.84, 134.60, 131.02, 127.51, 121.88, 108.96, 69.01, 56.61, 56.13, 55.52, 26.74, 25.03, 23.87; MS (EI) 231 (64, M), 203 (53), 202 (53), 174 (10), 161 (83), 148 (27), 121 (100), 120 (31); Anal. Calcd for C$_{14}$H$_{17}$NO$_2$: C, 72.70; H, 7.41; N, 6.06; found C, 72.47; H, 7.47; N, 5.91.

Example 7

1,3,4,11a-Tetrahydro-8chloro-2H-benzo[b]quinolizin-11(6H1)-one. By the above procedure, N-(3-chlorophenylmethyl)pipecolinic acid hydrochloride (Example 4, 901 mg) was converted to 1,3,4,11a-tetrahydro-8chloro-2H-benzo[b]quinolizin-11(6H)-one (451 mg) which was recrystallized from methanol: mp 106–108° C.; $^1$H NMR (300 MHz) δ 7.94 (d, J=8.4 Hz, 1 H), 7.32 (ddd, J=8.4, 2.0, 0.6 Hz, 1 H), 7.22 (m, 1 H), 3.82 (d, J=15.3 Hz, 1 H), 3.64 (d, J=15.3 Hz, 1 H), 3.06 (br d, J=11.4 Hz, 1 H), 2.76

(br d, J=10.5 Hz, 1 H), 2.36 (m, 2 H), 1.88 (m, 1 H), 1.30–1.70 (m, 4 H); $^{13}$C NMR (75 MHz) δ 194.85 (s), 143.70 (s), 139.77 (s), 128.68 (d), 128.65 (s), 127.82 (d), 126.15 (d), 68.97 (d), 56.69 (t), 56.01 (t), 26.58 (t), 24.97 (t), 23.70 (t); MS (EI) 235 (51, M), 206 (63), 165 (100); Anal. Calcd for $C_{13}H_{14}ClNO$: C, 66.24; H, 5.99; Cl, 15.04; N, 5.94; found C, 66.18; H, 6.02; Cl, 15.19; N, 5.85.

Example 8

1,3,4,11a-tetrahydro-2H-benzo[b]quinolizin-11(6H)one N-methylimine. A solution of the ketone of example 5 (1.10 g, 5.47 mmol) in $CH_2Cl_2$ (20 mL) was added to methylamine (5 mL) followed by the addition of $TiCl_4$ (2.74 mmol, 2.74 mL of 1.0 M solution in toluene). The mixture was stirred at room temperature for 10 h. It was filtered through a pad of diatomaceous earth (sold under the brand name CELITE) and rinsed with $CH_2Cl_2$. The filtrate was concentrated in vacuo to give a mixture of red solid and oil (1.29 g, 100%) which was directly used for the next step without purification.

Example 9 trans-N-Methyl-1,3,4,6,11,11a-hexahydro-11-amino-2H-benzo[b]quinolizine. The imine of example 8 (from 3.05 mmol ketone of example 5) was dissolved in THF (20 mL). LAH (380 mg) was added gradually to the mixture. The suspension was heated at reflux for 0.5 h and then stirred at room temperature for 10 h and quenched by the successive addition of $H_2O$ (380 µL), NaOH (aqueous, 15%, 380 µL) and $H_2O$ (1.1 mL). The mixture was filtered and the filtrate was concentrated to give trans-N-methyl-1,3,4,6,11,11a-hexahydro-11-amino-2H-benzo[b]quinolizine as a red oil (513 mg, 79% based on starting ketone): $^1$H NMR (300 MHz) δ 7.05–7.22 (m, 4 H), 4.00 (d, J=16.0 Hz, H-6), 3.34 (d, J=16.0 Hz, H-6), 3.24 (d, J=2.4 Hz, 1 H), 3.07 (br d, J=11.3 Hz, 1 H), 2.39 (dt, J=11.2, 2.8 Hz, 1 H), 2.36 (s, $CH_3$), 2.10 (m, 2 H), 1.94 (m, 1 H, NH), 1.83 (m, 1 H), 1.70 (m, 3 H), 1.33 (m, 1 H); $^{13}$C NMR (75 MHz) δ 136.26, 134.10, 128.88, 126.83, 126.23, 125.13, 61.80, 60.43, 58.32, 56.67, 34.36, 28.20, 25.57, 24.37; HCl salt mp: >230° C. (MeOH/2-PrOH/ether); MS (FAB), m/e 217 (100, M+H), 186 (36); HRMS (FAB) m/e calcd for $(C_{14}H_{20}N_2+H)$ 217.1705, found 217.1704; Anal. Calcd for $C_{14}H_{20}N_2.2HCl$: C, 58.14; H, 7.67; Cl, 24.51; N, 9.68. Found: C, 58.21; H, 7.86; Cl, 24.35; N, 9.58. The monohydrochloride salt (Example 9a) can be prepared by partial neutralization of the dihydrochloride.

Example 10 trans-N-Methyl-9-methoxy-1,3,4,6,11,11a-hexahydro11-amino-2H-benzo[b]quinolizine. In the same way the above compound was prepared, 1,3,4,11a-tetrahydro-9-methoxy-2H-benzo[b]quinolizin-11 (6H)one N-methyl imine was reduced to give an oil: $^1$H NMR (300 MHz) δ 6.97 (d, J=8.4 Hz, 1 H), 6.77 (dd, J=8.4 2.7 Hz, 1 H), 6.67 (d, J=2.6 Hz, 1 H), 3.93 (d, J=15.4 Hz, 1 H), 3.79 (s, $OCH_3$), 3.26 (d, J=15.3 Hz, 1 H), 3.18 (d, J=2.4 Hz, 1 H), 3.05 (br d, J=11.3 Hz, 1 H), 2.38 (s, $NCH_3$), 1.25–2.36 (m); $^{13}$C NMR δ 157.07, 137.61, 127.15, 126.18, 113.59, 112.89, 61.83, 60.75, 57.79, 56.68, 55.19, 34.57, 28.13, 25.56, 24.37; MS (FAB) 247 (100, M+H), 216 (88), 163 (66); HCl salt mp: >230° C. (MeOH/2-PrOH/ether); Anal. Calcd for $C_{15}H_{22}N_2.0.2HCl.0.2H_2O$: C, 55.80; H, 7.62; Cl, 21.96; N, 8.68; found C, 56.15; H, 7.59; Cl, 21.64; N, 8.56.

Example 11 trans-N-Methyl-8-chloro-1,3,4,6,11,11a-hexahydro-11-amino-2H-benzo[b]quinolizine. 1,3,4,11a-tetrahydro-8-chloro-2H-benzo[b]quinolizin-11(6H)one N-methylimine (1.06 g) was dissolved in THF (10 mL). Pt/C/S (410 mg) was added and the mixture was hydrogenated (50 psi) for 18 h at room temperature, then filtered and concentrated. The residue was chromatographed on silica gel eluting with $CH_2Cl_2$/MeOH/$NH_4OH$ (150/8/1) to give a red oil (287 mg): $^1$H NMR (300 MHz) δ 7.07 (m, 3 H), 3.93 (d, J=16.2 Hz, 1 H), 3.28 (d, J=16.5 Hz, 1 H), 3.22 (d, J=2.4 Hz, 1 H), 3.04 (br d, J=10.8 Hz, 1 H), 2.32 (s, CH3), 1.20–2.10 (m, 8 H); $^{13}$C NMR δ 135.93 (s), 134.54 (s), 132.35 (s), 130.13 (d), 126.03 (d), 125.29 (d), 61.51 (d), 59.64 (d), 57.79 (t), 56.43 (t), 34.01 (t), 27.93 (t), 25.39 (t), 24.17 (t); MS (FAB) 251 (78, M+H), 154 (100), 136 (77); HRMS (FAB) m/e calcd for $(C_{14}H_{19}ClN_2+H)$ 251.1315, found 251.1319. The amine was converted to the hydrochloride and crystallized from MeOH/2-Propanol/ether to give a gray solid: mp >230° C.; Anal. Calcd for $C_{14}H_{19}ClN_2.2HCl.0.2C_3H_8O$: C, 52.24; H, 6.79; Cl, 31.68; N, 8.34; found C, 52.04; H, 6.51; Cl, 31.36; N, 8.25.

Example 12 trans-N-Methyl-1,3,4,6,11,11a-hexhydro-11-amino-2H benzo[b]quinolizine. The imine of Example 8 (2.39 mmol, based on the starting ketone of Example 5) was dissolved in absolute ethanol (10 mL). Pd on carbon (10%, 210 mg) was added, and the mixture was hydrogenated in a shaker apparatus for 12 h at a pressure of 46 psi. The reaction mixture was filtered through CELITE. The filtrate was concentrated to give the compound of Example 9 as an oil (421 mg, 82% based on starting ketone) identical by $^1$H NMR to the sample obtained above by LAH reduction.

Example 13 trans-N-Benzyl-1,3,4,6,11,11a-hexahydro-11-amino-2H-benzo[b]quinolizine. Benzylamine (1.2 mL, 10.76 mmol) was added to a solution of the ketone of Example 5 (721 mg, 3.59 mmol) in $CH_2Cl_2$ (20 mL) followed by the addition of $TiCl_4$ (1.8 mmol, 1.8 mL of 1.0 M solution in toluene). The mixture was stirred at room temperature for 20 h. It was filtered through CELITE and the solid rinsed with $CH_2Cl_2$. The filtrate was concentrated in vacuo to give the N-benzylimine as a yellow solid, which was directly used for the next step without purification.

The benzylimine (189 mg) was dissolved in absolute ethanol (5 mL) and palladium on carbon (10%, 74 mg) was added. The mixture was hydrogenated in a shaker apparatus for 5 h at a pressure of 46 psi and then filtered through CELITE. The filtrate was concentrated to give a yellow oil (93 mg): $^1$H NMR (300 MHz) δ 7.01–7.40 (m, 9 H), 4.00 (d, J=15.9 Hz, 1 H), 3.86 (d, J=13.8 Hz, 1 H), 3.69 (d, J=13.5 Hz, 1 H), 3.336 (d, J=15.9 Hz, 1 H), 3.335 (d, J=1.8 Hz, 1 H), 3.08 (br d, J=11.4 Hz, 1 H), 1.25–2.42 (m, 8 H); $^{13}$C NMR (75 MHz) δ 141.17, 137.05, 134.17, 128.57, 128.24, 128.12, 126.66, 126.55, 126.31, 125.22, 62.15, 58.42, 57.36, 56.76, 59.92, 28.15, 25.65, 24.44; MS (FAB), m/e 293 (100, M+H), 209 (6), 198 (36), 186 (61), 91 (30); HRMS (FAB) m/e calcd for ($C_{20}H_{24}N_2$+H) 293.2018, found 293.2009. HCl salt was prepared from ethereal HCl solution and crystallized from MeOH/2-PrOH/ether: mp 185–188° C.; Anal. Calcd for $C_{20}H_{24}N_2$·HCl: C, 73.04; H, 7.66; Cl, 10.78; N, 8.52. Found: C, 72.73; H, 7.72; Cl, 11.11; N, 8.14.

Example 14 trans-N-Benzyl-9-methoxy-1,3,4,6,11,11a-hexahydro-11-amino-2H benzo[b]quinolizine. This compound was obtained as above from the corresponding imine (614 mg), as a brown oil (313 mg): $^1$H NMR (300 MHz) δ 7.20–7.40 (m, 5 H), 6.97 (d, J=8.7 Hz, 1 H), 6.76 (dd, J=8.4, 2.7 Hz, 1 H), 6.52 (d, J=2.7 Hz, 1 H), 3.97 (d, J=15.6 Hz, 1 H), 3.88 (d, J=13.5 Hz, 1 H), 3.76 (s, CH3O), 3.74 (d, J=13.5 Hz, 1 H), 3.32 (d, J=1.8 Hz, 1 H), 3.28 (d, J=15.6 Hz, 1 H), 3.09 (br d, J=11.1 Hz, 1 H), 1.30–2.40 (m, 8 H); $^{13}$C NMR (75 MHz) δ 157.27, 141.13, 138.07, 128.33, 128.21, 127.26, 126.65, 113.16, 57.83, 57.46, 56.79, 28.12, 25.60, 24.41; MS (FAB), m/e 323 (100, M+H), 239 (4), 216 (39), 108 (3), 91 (10). The HCl salt was prepared from ethereal HCl solution and crystallized from MeOH/2-PrOH: mp 213–215° C.; Anal. Calcd for $C_{21}H_{26}N_2O$·2HCl: C, 63.80; H, 7.14; Cl, 17.93; N, 7.09. Found: C, 63.83; H, 6.92; Cl, 17.47; N, 7.02.

Example 15 trans-1,3,4,6,11,11a-Hexahydro-11-amino-2H-benzo[b] quinolizine. Pd on carbon (10%, 154 mg) was added to a solution of trans-N-Benzyl-1,3,4,6,11,11a-hexahydro-11-amino-2H-benzo[b]quinolizine (93 mg) in THF (10 mL) and aqueous HCl (0.5 N, 1 mL). The mixture was hydrogenated in a shaker apparatus. Work-up as above gave a colorless oil (29 mg): $^1$H NMR (300 MHz) δ 7.00–7.25 (m, 4 H), 3.93 (d, J=15.7 Hz, 1 H), 3.58 (d, J=2.6 Hz, 1 H), 3.33 (d, J=15.7 Hz, 1 H), 3.01 (br d, J=11.3 Hz, 1 H), 2.32 (dt, J=10.8, 3.0 Hz, 1 H), 2.12 (td, J=11.6, 3.6 Hz, 1 H), 1.25–1.93 (m, 8 H); $^{13}$C NMR (75 MHz) δ 139.86, 133.60, 128.66, 126.73, 126.46, 125.85, 61.64, 58.60, 56.57, 53.11, 28.40, 25.70, 24.37; MS (FAB), m/e 203 (100, M+H), 186 (33), 84 (10); HRMS (FAB) m/e calcd for ($C_{13}H_{18}N_2$+H) 203.1548, found 203.1560; The hydrochloride was prepared with ethereal HCl and was crystallized from MeOH/2-PrOH/ether: mp >230° C.; Anal. Calcd for $C_{13}H_{18}N_2$·2HCl·$H_2O$: C, 53.25; H. 7.56; Cl, 24.18; N, 9.55. Found: C, 54.86; H, 7.69; Cl, 23.80; N, 9.32.

Example 16 cis-1,3,4,6,11,11a-hexahydro-11-amino-2H-benzo[b] quinolizine. (±)-α-Methylbenzylamine (0.99 mL, 7.70 mmol) was added to a solution of 1,3,4,11a-tetrahydro-2H-benzo[b]quinolizin-11(6H)-one (516 mg, 2.57 mmol) in $CH_2Cl_2$ (20 mL) followed by the addition of $TiCl_4$ (1.28 mmol, 1.28 mL of 1.0 M solution in toluene). The mixture was stirred at room temperature for 20 h. Hexanes (20 mL) was added and the suspension was filtered through CELITE. The filtrate was concentrated in vacuo to give a red oil (719 mg) which was directly used for the next step without purification.

Part of above oil (464 mg) was dissolved in MeOH (1 mL) and added to a $NaBH_4$ suspension in MeOH (4 mL) at 0° C. After 30 min., it was warmed to room temperature and stirred overnight. The reaction was quenched by the addition of water and MeOH was removed in vacuo. The residue was extracted with ether, dried ($Na_2SO_4$) and concentrated in vacuo to give an oil. The oil was dissolved in EtOH (5 mL) and HCl (3 N, 2 mL) and hydrogenated for 12 h in a shaker apparatus (50 psi) with catalysis by Pd/C (201 mg). The crude product was purified by chromatography (silica gel column eluting with $CH_2Cl_2$/MeOH/$NH_4OH$) to give cis-1,3,4,6,11,11a-hexahydro-11-amino-2H-benzo[b]quinolizine as a red oil (47 mg): $^1$H NMR (300 MHz) δ 7.51 (d, J=7.7 Hz, 1 H), 7.22 (d, J=7.4 Hz, 1 H), 7.15 (d, J=7.3 Hz, 1 H), 7.01 (d, J=7.5 Hz, 1 H), 3.78 (d, J=15.1 Hz, 1 H), 3.67 (d, J=8.6 Hz, 1 H), 3.43 (d, J=15.1 Hz, 1 H), 3.05 (br d, J=11.2 Hz, 1 H), 2.30 (m, 1 H), 2.16 (td, J=11.4, 3.9 Hz, 1 H), 1.24–1.96 (m, 8 H); $^{13}$C NMR (75 MHz) δ 138.54, 134.00, 126.84, 126.72, 126.41, 125.61, 67.60, 58.29, 56.20, 55.55, 30.89, 25.38, 24.11; MS (FAB), m/e 203 (100, M+H), 186 (45); HRMS (FAB) m/e calcd for ($C_{13}H_{18}N_2$+H) 203.1548, found 203.1531.

Example 17 cis-N-methyl-1,3,4,6,11,11a-hexahydro-2H-benzo[b] quinolizidin-11-amine. 1,3,4,11a-tetrahydro-2H-benzo[b] quinolizin-11(6H)one N-methylimine (1.29 g, 5.47 mmol based on starting ketone) was dissolved in absolute ethanol (20 mL). Sodium (2.23 g) was added in small pieces to maintain the reaction at reflux. After all the sodium was added, more ethanol (10 mL) was added to complete the reaction. The mixture was then cooled to 0° C. and water (10 mL) was slowly added. Ethanol was removed on a rotary evaporator. The residue was extracted with ether (4×40 mL), and the combined extracts were washed with brine (2×20 mL), dried ($Na_2SO_4$) and concentrated in vacuo to give a red oil (780 mg). $^1$H NMR showed that the product contained about 30% starting material. It was reduced again by the addition of sodium (1.43 g) to the solution of the oil in ethanol (20 mL). The reaction mixture was quenched by the addition of water (10 mL). Aqueous HCl (3 N, 50 mL) was added and the mixture was extracted with ether (50 mL). The aqueous layer was basified by the addition of solid NaOH, and was extracted with ether (3×50 mL). The combined extracts were dried and concentrated in vacuo to give a red oil (659 mg, 56%, cis:trans=3:2 by NMR). The mixture was separated by radial chromatography eluting with $CH_2Cl_2$/MeOH/$NH_4OH$ (150/8/1) to give two fractions (339 mg, cis:trans=3:2; 30 mg, cis:trans=9:1). The NMR spectrum of the latter fraction was obtained.

cis-N-methyl-1,3,4,6,11,11a-hexahydro-2H-benzo[b] quinolizidin-11-amine: $^1$H NMR (300 MHz) δ 7.39 (d, J=7.6 Hz, 1 H), 7.22 (t, J=7.3 Hz, 1 H), 7.14 (td, J=7.4, 1.0 Hz, 1 H), 7.03 (d, J=7.3 Hz, 1H), 3.72 (d, J=14.9 Hz, 1 H), 3.64 (d, J=8.4Hz, 1 H), 3.39 (d, J=15.1 Hz, 1 H), 3.05 (br d, J=11.3 Hz, 1 H), 2.30 (s, CH$_3$), 1.25–2.30 (m, 9 H); $^{13}$C NMR (75 MHz) δ 136.08, 135.48, 126.94, 126.61, 126.64, 125.84, 62.55, 61.86, 58.01, 56.32, 31.81, 31.05, 25.25, 24.23; MS (FAB), m/e 217 (100, M+H), 186 (29); HRMS (FAB) m/e calcd for ($C_{14}H_{20}N_2O$+H) 217.1705, found 217.1708.

Example 18 cis- and trans-1,3,4,6,11,11a-Hexahydro2H-benzo[b]quinolizidin-11-ol. A mixture of 1,3,4,11a-tetrahydro-2H-benzo[b]quinolizin-11(6H)-one (0.97 g, 4.83 mmol) and Pd/C (10%, 1.50 g) in THF (50 mL) and HCl (0.5 N, 5 mL) was hydrogenated in a shaker apparatus (45 psi) for 15 h. The mixture was basified with NaOH (2 N) and extracted with ether. The extract was dried ($Na_2SO_4$) and concentrated in vacuo to give a mixture of cis- and trans-1,3,4,6,11,11a-hexahydro-2H-benzo[b]quinolizidin-11-ol as a solid (790 mg). The solid was recrystallized from benzene to give the cis isomer (410 mg) as a colorless solid, mp 158–160° C. (lit.[6] 162° C.). The mother liquor was evaporated and the residue was crystallized from ethanol to give the trans isomer (132 mg) as a colorless solid, mp 152–154° C.

Example 18a cis-1,3,4,6,11,11a-hexahydro-2H-benzo[b]quinolizidin-11-ol $^1$H NMR (300 MHz) δ 7.52 (d, J=7.3 Hz, 1 H), 7.22 (m, 2 H), 7.03 (d, J=7.3 Hz, 1 H), 4.47 (d, J=8.4 Hz, 1 H), 3.81 (d, J=15.3 Hz, 1 H), 3.44 (d, J 15.3 Hz, 1 H), 3.04 (br d, J=11.3 Hz, 1 H), 2.33 (m, 1 H), 2.18 (td, J=11.5, 3.9 Hz, 1 H), 2.07 (m, 1 H), 1.30–1.90 (m, 6 H).

Example 18b trans-1,3,4,6,11,11a-hexahydro-2H-benzo[b]quinolizidin-11-ol: $^1$H NMR (300 MHz) δ 7.35 (m, 1 H), 7.22 (m, 2 H), 6.94 (m, 1 H), 4.12 (s, 1 H), 3.56 (s, OH), 3.39 (d, J=15.7 Hz, 1 H), 3.16 (d, J=15.6 Hz, 1 H), 2.93 (br d, J=10.9 Hz, 1 H), 2.24 (dt, J=11.2, 2.7 Hz, 1 H), 1.20–2.10 (m, 7 H); $^{13}$C NMR (75 MHz) δ 137.11, 134.04, 129.41, 127.54, 126.52, 126.08, 69.67, 62.39, 58.02, 56.14, 27.36, 25.23, 24.07; MS (FAB), m/e 204 (100, M+H), 186 (40), 84 (50); Anal. Calcd for $C_{13}H_{17}NO$: C, 76.81; H, 8.43; N, 6.89. Found: C, 76.94; H, 8.49; N, 6.74.

Example 19

O-acetyl-cis-1,3,4,6,11,11a-hexahydro-2H-benzo[b]quinolizidin-11-ol. A solution of acetyl chloride (238 μL, 3.34 mmol) in $CH_2Cl_2$ (2 mL) was added to a solution of cis-1,3,4,6,11,11a-hexahydro-2H-benzo[b]quinolizidin-11-ol (563 mg, 2.78 mmol) and $Et_3N$ (465 μL, 3.34 mmol) in $CH_2Cl_2$ (10 mL) at 0° C. The mixture was stirred at room temperature for 2 h and then diluted with $CH_2Cl_2$ (50 mL). The solution was washed with $Na_2CO_3$ (sat., 10 mL) and $H_2O$(10 mL), dried ($Na_2SO_4$) and concentrated in vacuo. The residue was chromatographed on silica gel column eluting with $CHCl_3$/MeOH/$NH_4OH$ (99/0.8/0.2) followed by crystallization (EtOAc/Hexanes) to give O-acetyl-cis-1,3,4,6,11,11a-hexahydro-2H-benzo[b]quinolizidin-11-ol as a yellow solid: mp 116–117° C.; $^1$H NMR (300 MHz) δ 7.03–7.22 (m, 4 H), 5.97 (d, J=8.6 Hz, H-11), 3.82 (d, J=15.3 Hz, H-6), 3.49 (d, J=15.1, H-6), 3.06 (br d, J=11.2 Hz, 1 H), 2.20–2.35 (m, 2 H), 2.17 (s, $CH_3$), 1.64–1.96 (m, 3 H), 1.25–1.47 (m, 3 H); 13C NMR (75 MHz) δ 171.16, 135.06, 132.43, 129.56, 128.35, 126.73, 125.80, 70.00, 61.21, 58.09, 56.48, 27.40, 25.36, 24.07, 21.24; MS (EI), m/e 246 (87, M+H), 186 (100); Anal. Calcd for $C_{15}H_{19}NO_2 \cdot 0.1H_2O$: C, 72.91; H, 7.83; N, 5.67. Found: C, 72.87; H, 7.73; N, 5.60.

Example 20

Oacetyl-trans-1,3,4,6,11,11a-hexahydro-2H-benzo[b]quinolizidin-11-ol. Acetyl chloride (82 mg, 1.05 mmol) was added to trans-1,3,4,6,11,11a-hexahydro-2H-benzo[b]quinolizidin-11-ol (193 mg, 0.95 mmol) as described in Example 19, to give O-acetyl-trans-1,3,4,6,11,11a-hexahydro-2H-benzo[b]quinolizidin-11-ol as a yellow solid (59 mg): mp 92–94° C.; $^1$H NMR (300 MHz) δ 7.16–7.34 (m, 3 H), 7.07 (d, J=7.4 Hz, 1 H), 5.98 (d, J=2.8 Hz, H-11), 4.00 (d, J=15.6 Hz, H-6), 3.35 (d, J=15.6, H-6), 3.19 (br d, J=11.5 Hz, 1 H), 2.45 (dt, J=10.8, 3.1 Hz, 1 H), 2.11 (s, $CH_3$), 1.85 (m, 1 H), 1.50–1.75 (m, 5 H), 1.35 (m, 1 H); $^{13}$C NMR (75 MHz) δ 171.16, 135.06, 132.43, 129.56, 128.35, 126.73, 125.80, 70.00, 61.21, 58.09, 56.48, 27.40, 25.36, 24.07, 21.24; MS (EI), m/e 244 (6, M–H), 202 (54), 185 (100), 156 (23), 129 (15), 120 (60); HRMS (EI) m/e calcd for ($C_{15}H_{19}NO_2$–H) 244.1338, found 244.1330; Anal. calc. for $C_{15}H_{19}NO_2 \cdot H_2O$: C, 72.91; H, 7.83; N, 5.67. Found: C, 72.81; H, 7.56; N, 5.56.

Example 21

N-butyryl-trans-1,3,4,5,11,11a-hexahydro-11-amino-2H-benzo[b]quinolizine. Butyryl chloride (2.82 mmol, 295 μL) in $CH_2Cl_2$ (5 mL) was added dropwise to a solution of trans-1,3,4,6,11,11a-hexahydro-11-amino-2H-benzo[b]quinolizine (2.56 mmol, 518 mg) and triethylamine (2.82 mmol, 393 μL) in $CH_2Cl_2$ (40 mL). The mixture was stirred overnight at room temperature. Saturated $Na_2CO_3$ solution (10 mL) was added and the aqueous layer was extracted with additional $CH_2Cl_2$ (2×30 mL). The combined extracts were dried ($Na_2SO_4$) and concentrated. The residue was chromatographed on silica gel eluting with $CH_2Cl_2$/MeOH/$NH_4OH$ (150/8/1) to give N-butyryl-trans-1,3,4,5,11,11a-hexahydro-11-amino-2H-benzo[b]quinolizine as a brown solid (299 mg): mp 141–143° C.; $^1$H NMR (300 MHz) b 7.34 (dd, J=6.6, 2.4 Hz, 1 H), 7.14–7.23 (m, 2 H), 7.02 (dd, J=6.6, 2.1 Hz, 1 H), 6.10 (d, J=9.6 Hz, 1 H), 5.06 (dd, J=9.9, 2.7 Hz, 1 H), 3.92 (d, J=15.6 Hz, 1 H), 3.37 (d, J=15.6 Hz, 1 H), 3.09 (br d, J=11.4 Hz, 1 H), 2.44 (dt, J=10.8, 3.0 Hz, 1 H), 2.40 (m, 3 H), 1.25–1.80 (m, 8 H), 0.91 (t, J=7.4 Hz, 3 H); $^{13}$C NMR (75 MHz) δ 171.98, 135.98, 133.78, 129.19, 127.36, 126.75, 125.67, 60.78, 58.46, 56.37, 49.48, 38.85, 27.89, 25.57, 23.86, 19.21, 13.75; MS (FAB), m/e (100, M+H); Anal. Calcd for $C_{17}H_{24}N_2O$: C, 74.96; H, 8.88; N, 10.28. Found: C, 74.85; H, 8.67; N, 10.01.

Example 22

Pyrrolidine-2-one-1-acetic acid. A solution of methyl pyrrolidine-2-one-1-acetate (10 mmol, 1.57 g) in THF (20 mL) and NaOH (1 N, 10 mL) was stirred at room temperature for 24 hours. The mixture was acidified by the addition of HCl (1 N) and extracted with $CHCl_3$ (3×20 mL). The combined extracts were dried ($Na_2SO_4$) and concentrated in vacuo to give pyrrolidine-2-one-1-acetic acid as a colorless solid: mp 140–142° C.; $^1$H NMR (300 MHz) δ 8.92 (br s, OH), 4.09 (s, 2 H), 3.53 (t, J=7.1 Hz, 2 H), 2.48 (t, J=8.1 Hz, 2 H), 2.10 (quin, J=7.5 Hz, 2 H); $^{13}$C NMR (75 MHz) δ 176.72, 171.59, 48.13, 44.19, 30.35, 17.90; MS (FAB), m/e 144 (100, M+H), 98 (19); Anal. Calcd for $C_6H_9NO_3$: C, 50.35; H, 6.34; N, 9.79. Found: C, 49.99; H, 6.21; N, 9.78.

Example 23

N-[(2oxopyrrolidinyl)acetyl]-trans-1,3,4,6,11,11a-hexahydro-11-amino-2H-benzo[b]quinolizine: A mixture of pyrrolidine-2-one-1-acetic acid (2.52 mmol, 360 mg) and carbonyldiimidazole (2.52 mmol, 408 mg) in THF (20 mL) was stirred at room temperature for 2 hours. A solution of trans-1,3,4,6,11,11a-hexahydro-11-amino-2H-benzo[b] quinolizine in THP (5 mL) was added in 5 min. The mixture was stirred at room temperature for 40 hours. It was acidified by the addition of HCl (0.5 N, 20 mL) and washed with ether (2×30 mL). The aqueous layer was basified by the addition of solid NaOH, and extracted with ether (3×50 mL). The combined extracts were dried ($Na_2SO_4$) and concentrated to give a brown solid. The solid was washed with ethyl acetate to give an off-white solid (387 mg): mp 174–176° C. (EtOAc); $^1$H NMR (300 MHz) δ 7.32 (br d, J=7.4 Hz, 1 H), 7.13–7.23 (m, 2 H), 7.02 (br d, J=6.9 Hz, 1 H), 6.46 (d, J=9.6 Hz, NH), 4.97 (dd, J=9.6, 2.4 Hz, 1 H), 3.83–4.00 (m, 3 H), 3.36–3.54 (m, 2 H), 3.36 (d, J=15.6 Hz, 1 H), 3.08 (br d, J=11.1 Hz, 1 H), 1.26–2.49 (m, 12 H); $^{13}$C NMR (75 MHz) δ 175.56, 166.91, 135.52, 133.94, 128.97, 127.55, 126.69, 125.79, 60.34, 58.35, 56.15, 50.05, 48.01, 46.72, 30.33, 27.87, 25.55, 23.80, 17.97; MS (FAB), m/e 328 (100, M+H), 185 (38); Anal. Calcd for $C_{19}H_{25}N_3O_2$: C, 69.70; H, 7.70; N, 12.83. Found: C, 69.46; H, 7.73; N, 12.69.

Example 24.

1,2,3,5,10,10a-hexahydropyrrolo[1,2-b]isoquinolin-3,10dione (Rigo, B.; Kolocouris, N. *J. Heterocyclic. Chem.* 1983, 20, 893): A mixture of N-benzyl-pyrrolidin-2-one-4-carboxylic acid (3.7 mmol, 860 mg), thionyl chloride (8 mL) and pyridine (1 drop) was heated at 65–70° C. for 20 min. The pale yellow solution was evaporated in vacuo. The resulting acid chloride was dissolved in benzene (16 mL) and added within 30 min to a suspension of $AlCl_3$ (122 mmol, 16.3 g) in benzene (40 mL). The suspension was heated at 55° C. for 30 min and then at 65° C. for 5 min. The mixture was then cooled and hydrolyzed with a minimum amount of water and ice. The aqueous phase was extracted with $CH_2Cl_2$ (2×30 mL). The organic phase was washed with water, aqueous NaOH (1 N) and more water, dried with $Na_2SO_4$ and concentrated in vacuo to give an oil. Acetone and ether was added to the oil and precipitate formed overnight. The precipitate was filtered and dried in vacuo to give 1,2,3,5,10,10a-hexahydropyrrolo[1,2-b]isoquinolin-3,10-dione acid as a yellow solid (557 mg): mp 105–107° C. (lit. mp 107–108° C.); $^1$H NMR (300 MHz) δ 8.09 (dd, J=7.8, 0.9 Hz, 1 H), 7.60 (td, J=7.5, 1.3 Hz, 1 H), 7.42 (t, J=7.6 Hz, 1 H), 7.33 (d, J=7.7 Hz, 1 H), 5.28 (d, J=17.5 Hz, 1 H), 4.37 (d, J=17.5 Hz, 1 H), 4.32 (m, 1 H), 2.50 (m, 4 H); $^{13}$C NMR (75 MHz) δ 194.03, 173.79, 139.62, 134.36, 130.08, 127.71, 127.59, 126.42, 61.64, 41.32, 29.78, 20.45.

Example 25

10-Methylimino-1,2,3,5,10,10a-hexahydropyrrolo[1,2b]isoquinolin-3one. Methylamine (1 mL) was condensed at −78° C. into a flask containing 1,2,3,5,10,10a-hexahydropyrrolo[1,2-b]isoquinolin-3,10-dione (5.54 mmol, 1.113 g). $CH_2Cl_2$ (30 mL) was added, and $TiCl_4$ (2.77 mmol, 2.77 mL of 1 M solution in toluene) was gradually added and the mixture was warmed up to room temperature and stirred for 20 hours. Petroleum ether (20 mL) was added and then the mixture was filtered through CELITE. The filtrate was concentrated in vacuo to give 10-methylimino-1,2,3,5,10,10a-hexahydropyrrolo[1,2-b]isoquinolin-3-one as a red oil (1.28 g).

Example 26a trans-10-Methylamino-1,2,3,5,10,10a-hexahydropyrrolo[1,2-b]isoquinolin-3-one. A mixture of 10methylimino-1,2,3,5,10,10a-hexahydropyrrolo[1,2-b]isoquinolin-3-one (159 mg) and Pd/C (10%, 110 mg) in EtOH (10 mL) was hydrogenated in a shaker apparatus at 50 psi overnight, and then filtered. The filtrate was concentrated in vacuo and the residue was chromatographed on silica gel eluting with $CH_2Cl_2$/MeOH/NH4OH (150/8/1) to give an oil (11 mg): $^1$H NMR (300 MHz) δ 7.25 (m, 4 H), 4.92 (d, J=18.0 Hz, 1 H), 4.31 (d, J=17.7 Hz, 1 H), 3.95 (m, 1 H), 3.43 (d, J=2.7 Hz, 1 H), 2.38 (s, NCH3); MS (FAB), m/e 217 (100, M+H), 154 (55), 136 (45).

Example 26b cis-10Methylamino-1,2,3,5,10,10a-hexahydropyrrolo[1, 2b]isoquinolin-3-one. A solution of 10-methylimino-1,2,3, 5,10,10a-hexahydropyrrolo[1,2-b]isoquinolin-3-one (800 mg, 3.7 mmol) in absolute ethanol (13 ml) was cooled to 0° C. Solid sodium borohydride (560 mg, 14.8 mmol) was added in portions over 30 min, and the mixture was then stirred at room temperature for 18 hr. The reaction was quenched by addition of water (50 ml), and extracted with $CH_2Cl_2$ (4×20 ml). The extracts were washed with brine (50 ml), dried ($Na_2SO_4$), filtered, and concentrated to provide 677 mg of a viscous residue. Chromatography on silica gel with $CH_2Cl_2$/MeOH/$NH_4$OH (95:4:1) provided the product as a pale yellow oil (424 mg, 53%) that crystallized on standing, mp 88–90° C. $^1$H NMR (300 MHz, $CDCl_3$) δ 7.53 (d, J=7.22 Hz, 1 H), 7.25 (m, 2H), 7.16 (d, J=6.85 Hz, 1H), 4.92 (d, J=17.45 Hz, 1 H), 4.24 (d, J=17.45 Hz, 1 H), 3.70 (m, 1 H), 3.65 (d, J=9.46 Hz, 1 H), 2.50–2.40 (m, 3H), 2.48 (s, 3H, NCH3); IR (neat) 3430, 3345, 1670, 1655, 1575, 1283, 1093, 1080, 975, 749 cm$^{-1}$; MS (FAB), m/e 217 (100%, M+H), 186 (41%), 154 (15%), 133 (27%), 118 (14%); HRMS (FAB) calc. for $C_{13}H_{17}N_2O$(M+H) 217.1341, found 217.1359; Anal. calc for $C_{13}H_{16}N_2O$ C 72.19%, H 7.46%, N 12.95%, found C 72.11%, H 7.33%, N 12.88%. Approximately 10% of the trans isomer was observed in the NMR spectrum (benzylic doublet at δ 3.45, J=2.63 Hz).

Example 27

Diisopropyl glutamate. (Buckley III, T. F.; Rapoport, H. *J. Org. Chem.* 1984, 48, 4222) Concentrated sulfuric acid (11 mL) was added to a suspension of d,l-glutamic acid (0.17 mol, 25 g) in 2-propanol/toluene (675 mL, 1/1). The solution was refluxed for 24 hours using a Soxhlet apparatus containing 3 Å molecular sieves, and then evaporated to approximately 100 mL. The residue was diluted with cold saturated $NaHCO_3$ (300 mL), adjusted to pH 9.5 and extracted with $CH_2Cl_2$ (4×150 mL). The combined extracts were dried over $Na_2SO_4$ and concentrated in vacuo to give diisopropyl glutamate as an oil (38.6 g): $^1$H NMR (Buckley III, T. F.; Rapoport, H. *J. Org. Chem.* 1984, 48, 4222) (300 MHz) δ 5.04 (heptet, J=6.3 Hz, 1 H), 5.01 (heptet, J=6.3 Hz, 1 H), 3.41 (dd, J=8.6, 5.3 Hz, 1 H), 2.42 (t, J=7.7 Hz, 2 H), 2.05 (m, 1 H), 1.82 (m, 1 H), 1.26 (d, J=6.3 Hz, 6 H), 1.23 (d, J=6.3 Hz, 6 H); $^{13}$C NMR (75 MHz) δ 175.14, 172.67, 68.47, 67.72, 53.87, 31.00, 29.84, 21.78.

Example 28

N-benzyl diisopropyl glutamate. A mixture of diisopropylglutamic acid (0.167 mol, 38.6 g), benzyl chloride (0.184 mmol, 21.1 mL) and $K_2CO_3$ (0.20 mol, 27.7 g) in DMF (110 mL) was heated at 62° C. for 4 days. The mixture was filtered, the filtrate was acidified by addition of aqueous HCl (1.5 N), and extracted with ether (3×50 mL). The aqueous layer was basified with NaOH and extracted with ether. The ether extract was dried ($Na_2SO_4$ and $MgSO_4$) and concentrated in vacuo to give N-benzyl diisopropyl glutamate as a yellow oil which was contaminated with DMF: $^1$H NMR (300 MHz) δ 7.32 (m, 5 H), 5.07 (heptet, J=6.3 Hz, 1 H), 4.98 (heptet, J=6.3 Hz, 1 H), 3.82 (d, J=12.9 Hz, 1 H), 3.61 (d, J=12.9 Hz, 1 H), 3.21 (dd, J=8.4, 5.5 Hz, 1 H), 2.33–2.51 (m, 2 H), 1.78–2.03 (m, 3 H), 1.27 (d, J=6.3 Hz, 3 H), 1.26 (d, J=6.3 Hz, 3 H), 1.21(0) (d, J=6.3 Hz, 3 H), 1.20(6) (d, J=6.3 Hz, 3 H); $^{13}$C NMR (75 MHz) δ 174.38, 172.58, 139.85, 128.24, 128.12, 126.93, 68.21, 67.52, 60.03, 51.95, 31.12, 28.33, 21.86, 21.72; MS (FAB), m/e 322 (100, M+H), 234 (25); HRMS (FAB) m/e calcd for ($C_{18}H_{27}NO_4$+H) 322.2018, found 322.2029.

Example 29

Isopropyl N-benzylpyrrolidin-2-one-4-carboxylate. A solution of N-benzyl diisopropyl glutamate (0.020 mol, 6.43 g) in MeOH (100 mL) and acetic acid (50 mL) was stirred at 45° C. for 3 h. The mixture was evaporated in vacuo to give isopropyl N-benzylpyrrolidin-2-one-4-carboxylate as a yellow oil (3.93 g): $^1$H NMR (300 MHz) δ 7.20–7.40 (m, 5 H), 5.07 (d, J=14.8 Hz, 1 H), 5.02 (heptet, J=6.3 Hz, 1 H), 3.95 (d, J=14.2 Hz, 1 H), 3.92 (dd, J=9.1, 3.2 Hz, 1 H), 1.99–2.64 (m, 4 H), 1.24 (d, J=6.3 Hz, 3 H), 1.23 (d, J=6.3 Hz, 3 H); $^{13}$C NMR (75 MHz) δ 175.07, 171.21, 135.85, 128.69, 128.49, 127.74, 69.16, 58.95, 45.57, 29.55, 22.82, 21.69, 21.62; MS (FAB), m/e 262 (100, M+H), 174 (20); HRMS (FAB) m/e calcd for ($C_{15}H_{19}NO_3$+H) 262.1443, found 262.1420.

Example 30

N-Benzylpyrrolidin-2-one-4-carboxylic acid. A mixture of isopropyl N-benzylpyrrolidin-2-one4-carboxylate (Example 33, 3.93 g) in dioxane (80 mL), aqueous KOH (2 N, 40 mL) and MeOH (60 mL) was stirred at room temperature for 1 hour. The mixture was then cooled with ice, acidified to pH=4 with $H_3PO_4$ and left in a refrigerator overnight. The precipitate was filtered and the filtrate was concentrated to give a yellow oil. The oil was contaminated with dioxane, and therefore was dissolved in aqueous KOH. The solution was extracted with $CHCl_3$ (2×20 mL), and the aqueous layer was acidified with HCl (3 N). It was extracted with $CHCl_3$ (4×30 mL). The combined extracts were dried ($Na_2SO_4$) and concentrated in vacuo to give N-benzylpyrrolidin-2-one-4carboxylic acid as a pale yellow oil (2.89 g): $^1$H NMR (300 MHz) δ 10.77 (br s, $CO_2$H), 7.34 (m, 5 H), 5.17 (d, J=14.9 Hz, 1 H), 4.02 (dd, J=9.4, 3.2Hz, 1 H), 3.98 (d, J=14.1 Hz, 1 H), 2.12–2.71 (m, 4 H); $^{13}$C NMR (75 MHz) δ 176.47, 174.32, 135.25, 128.78, 128.46, 127.90, 58.63, 45.69, 29.57, 22.83; MS (FAB), m/e 220 (100, M+H), 174 (40); HRMS (FAB) m/e calcd for ($C_{12}H_{13}NO_3$+H) 220.0974, found 220.0984.

Example 31

N-Benzylpyrrolidin-2-one-5-carboxylic acid. [a) Ohfune, Y.; Kurokawa, N.; Higuchi, N.; Saito, M.; Hashimoto, M.; Tanaka, T. Chem Lett. 1984, 441. b) Peterson, J. S.; Fels, G.; Rapoport, H. J. Am. Chem. Soc. 1984, 106, 4539] Benzaldehyde (0.30 mol, 30.5 mL) was added dropwise to a suspension of d,l-glutamic acid (0.20 mol, 33.0 g) and $NaBH_3CN$ (0.30 mol, 18.9 g) in methanol (600 mL) at room temperature. The mixture was stirred at room temperature for 18 hours. The white precipitate was filtered and washed with MeOH. The solid was dried under vacuum to give a colorless solid (14.5 g) which was a 1:1 mixture of N-benzylglutamic acid and glutamic acid by $^1$H NMR. The mixture was not separated and was subjected to the next step directly.

The above mixture was suspended in water (100 mL) and refluxed for 20 hours. The solid dissolved 30 minutes after refluxing. The solution was extracted with $CHCl_3$ (3×100 mL). The combined extracts were washed with brine (30 mL), dried ($Na_2SO_4$) and concentrated to give N-benzylpyrrolidin-2-one-5-carboxylic acid as a colorless solid (7.1 g). The $^1$H NMR spectrum was identical to that obtained with the sample from the above procedure.

Example 32

10-Ethylenedioxy-1,2,3,5,10,10a-hexahydropyrrolo[1,2-b]isoquinoline. This compound was prepared from 1,2,3,5,10,10a-hexahydropyrrolo[1,2-b]isoquinolin-3,10-dione as described (Rigo, B.; Kolocouris, N. J. Heterocyclic. Chem. 1983, 20, 893). $^1$H NMR (300 MHz) δ 7.46 (dd, J=5.4, 3.8 Hz, 1 H), 7.23 (m, 2 H), 7.07 (dd, J=5.4, 3.7 Hz, 1 H), 4.36 (td, J=12.2, 3.6 Hz, 1 H), 4.05–4.24 (m, 4 H), 3.43 (d, J=14.7 Hz, 1 H), 3.27 (m, 1 H), 2.66 (t, J=7.5 Hz, 1 H), 2.32 (q, J=8.1 Hz, 1 H), 1.70–2.00 (m, 4 H); $^{13}$C NMR (75 MHz) δ 137.66, 136.19, 128.03, 126.40, 125.88, 125.79, 106.68, 68.06, 66.56, 65.69, 55.62, 54.72, 23.80, 21.66; MS (FAB), m/e 232 (100, M+H), 188 (60); 170 (53).

Example 33

1,2,3,5,10,10a-Hexahydropyrrolo[1,2-b]isoquinolin-10-one (Method A) The compound was prepared from 10-ethylenedioxy-1,2,3,5,10,10a-hexahydropyrrolo[1,2-b]isoquinoline as described previously (Rigo, B.; Kolocouris, N. J. Heterocyclic. Chem. 1983, 20, 893). $^1$H NMR (300 MHz) δ 8.05 (dd, J=7.9, 0.9 Hz, 1 H), 7.48 (td, J=7.7, 1.3 Hz, 1 H), 7.22–7.36 (m, 2 H), 4.20 (d, J=15.2 Hz, 1 H), 3.71 (d, J=15.1 Hz, 1 H), 3.22 (dt, J=8.7, 4.5 Hz, 1 H), 2.93 (td, J=8.2, 1.8 Hz, 1 H), 2.48 (q, J=8.7 Hz, 1 H), 2.14 (m, 2 H), 1.85 (m, 2 H); $^{13}$C NMR (75 MHz) δ 196.07, 142.40, 133.18, 131.09, 127.01, 126.80, 126.45, 69.39, 54.66, 54.11, 24.65, 21.31; MS (FAB), m/e 186 (100, M–H), 154 (40), 136 (32).

(Method B) Jones reagent (1.1 equiv., 1.77 mmol, 0.663 mL) was added to a solution of cis-1,2,3,5,10,10a-hexahydropyrrolo[1,2-b]isoquinolin-10-ol (1.61 mmol, 304 mg, Example 35 below) in acetone (10 mL) in 5 minutes at room temperature (Szmuszkovicz, J.; Skaletzky, L. L. J. Org. Chem. 1967, 32, 3300). The mixture was concentrated in vacuo and $H_2O$(15 mL) was added. The mixture was cooled with ice, basified with NaOH (10 mL, 1 N) and extracted with $CH_2Cl_2$ (3×20 mL). The combined extracts were washed with $H_2O$(15 mL) and brine (15 mL), dried over $Na_2SO_4$ and concentrated in vacuo to give 1,2,3,5,10,10a-hexahydropyrrolo[1,2-b]isoquinolin-10-one as a yellow oil (198 mg). The $^1$H NMR spectrum was identical to that obtained by method (A).

Example 34a cis-10-methylamino1,2,3,5,10,10a-hexahydropyrrolo[1,2-b]isoquinoline. Anhydrous methylamine (36 drops) was condensed into a flask containing 1,2,3,5,10,10a-hexahydropyrrolo[1,2-b]isoquinolin-3,10-dione (1.76 g, 8.80 mmol), to give a brown suspension. The suspension was cooled to −78° C., and anhydrous $CH_2Cl_2$ (44 mL) was added. $TiCl_4$ (4.4 mmol, 4.4 mL of 1.0 M solution in toluene) was added dropwise with efficient stirring. The mixture was stirred at −78° C. for 30 min, and then at room temperature for 22 hours. Petroleum ether (20 mL) was added, and the mixture was then poured into 80 ml petroleum ether. The mixture was filtered through CELITE and the filtrate was concentrated in vacuo to give 10-methylimino-1,2,3,5,10,10a-hexahydropyrrolo[1,2-b]isoquinolin-3-one(23, $R^1=R^3=R^4=H$; $R^6=Me$) as a viscous amber residue (1.63 g): $^1$H NMR ($CDCl_3$, 300 MHz) δ 8.00 (d, 1H), 7.44–7.15 (m, 3H), 5.14 (d, 1H), 4.87 (m, 1H), 4.04 (d, 1H), 3.45 (s, 3H), 2.79 (m, 1H), 2.56 (m, 1H), 1.90 (m, 1H).

The 10-methylimino-1,2,3,5,10,10a-hexahydropyrrolo[1,2-b]isoquinolin-3-one (880 mg, 4.1 mmol) was dissolved in THF (12 mL) and added dropwise to a suspension of LAH (623 mg, 16.4 mmol) in THF (12 ml) at room temperature under nitrogen. The suspension was stirred at reflux for 15 hours, cooled, and quenched by the addition of $H_2O$(0.88 mL), NaOH (1.5 N, 0.88 mL) and additional $H_2O$(2.6 mL). The mixture was filtered and the filtrate was concentrated in vacuo to give cis-10-methylamino-1,2,3,5,10,10a-hexahydropyrrolo[1,2-b]isoquinoline as a dark oil (600 mg). Chromatography on silica gel with CH2Cl2/MeOH/NH4OH (95:4:1) provided the product as a dark red, viscous oil (547 mg). $^1$H NMR ($CDCl_3$, 300 MHz): δ 7.52 (d, J=7.63 Hz, 1H), 7.25 (t, J=7.23, 14.47 Hz, 1H), 7.17 (t, J=7.76, 15.13 Hz, 1H), 7.09 (d, J=7.63 Hz, 1H), 4.03 (d, J=14.01 Hz, 1H), 3.79 (d, J=10.01 Hz, 1H), 3.62 (d, J=14.01 Hz, 1H), 3.17 (m, 1H), 2.58 (m, 1H), 2.47 (m, 1H), 2.41 (s, 3H), 2.28 (m, 1H), 1.87 (m, 1H0, 1.69 (m, 1H); $^{13}$C NMR ($CDCl_3$): δ 137.24, 135.83, 126.63, 126.20 (2C), 64.92, 62.70, 55.85, 54.71, 32.33, 30.04, 21.57; IR (neat): 3285 (br), 3060, 3020, 2950, 2870, 2795, 1735–1565 (br), 1475, 1450, 1155, 1035, 920, 905, 780, 720 cm$^{-1}$; MS (FAB): m/e 203 (M+H, 74.8%), 201 (74.1%), 172 (M−NHMe, 100%), 170 (85%), 133 (53.1%), 132 (27%), 118 (17.7%); HRMS (FAB): Calc for $C_{13}H_{18}N_2$ 202.1469, found 203.1555 (M+H).

Example 34b trans-10-methylamino-1,2,3,5,10,10a-hexahydropyrrolo[1,2-b]isoquinoline. The imine 10-methylimino-1,2,3,5,10,10a-hexahydropyrrolo[1,2-b]isoquinolin-3-one was prepared as described in Example 34a above. To a solution of this imine (159 mg) in ethanol (10 ml) was added 10% Pd on carbon (110 mg), and the mixture was hydrogenated under 50 psi hydrogen overnight. The mixture was filtered through CELITE, the filtrate was concentrated in vacuo, and the residue was chromatographed on silica gel with CH2Cl2/MeOH/NH4OH (150:8:1) to provide trans-10-methylamino-1,2,3,5,10,10a-hexahydropyrrolo[1,2-b]isoquinoline as an oil (11 mg). $^1$H NMR ($CDCl_3$, 300 MHz): δ 7.25 (m, 4H), 4.92 (d, J=18.0 Hz, 1H0, 4.31 (d, J=17.7 Hz, 1H), 3.95 (m, 1H), 3.43 (d, J=2.7 Hz, 1H), 2.38 (s, 3H); MS (FAB) m/e 217 (100%, M+H), 154 (55%), 136 (45%).

Example 35 cis-1,2,3,5,10,10a-hexahydropyrrolo[1,2-b]isoquinolin-10-ol. A solution of 1,2,3,5,10,10a-hexahydropyrrolo[1,2-b]isoquinolin-3,10-dione in THF (20 mL) was added to a suspension of LAH (7.95 mmol, 302 mg) in THF (10 mL). The mixture was refluxed for 16 hours and then quenched by the addition of $H_2O$ (0.3 ML), NaOH (15%, 0.3 mL) and additional $H_2O$ (0.9 mL). The precipitate was filtered and the filtrate was concentrated in vacuo. The residue was chromatographed on silica gel eluting with $CH_2Cl_2$/MeOH/$NH_4OH$ (150/8/1) to give cis-1,2,3,5,10,10a-hexahydropyrrolo[1,2-b]isoquinolin-10-ol as an off-white solid (178 mg): mp 131–133° C. (lit (Rigo, B.; Kolocouris, N. J. Heterocyclic. Chem. 1983, 20, 893) mp 135–136° C.); $^1$H NMR (300 MHz) δ 7.52 (br d, J=7.2 Hz, 1 H), 7.16–7.25 (m, 2 H), 7.02 (br d, J=6.9 Hz, 1 H), 4.46 (d, J=8.4 Hz, 1 H), 3.97 (d, J=14.7 Hz, 1 H), 3.38 (d, J=14.7 Hz, 1 H), 3.18 (td, J=8.4, 2.4 Hz, 1 H), 2.56 (br s, OH), 1.60–2.32 (m, 6 H); $^{13}$C NMR (75 MHz) δ 138.53, 134.70, 127.01, 126.71, 126.46, 125.91, 73.59, 67.50, 55.45, 54.67, 29.12, 21.55; MS (FAB), m/e 190 (100, M+H), 172 (30), 119 (15); HRMS (FAB) m/e calcd for ($C_{12}H_{15}NO$+H) 190.1232, found 190.1228.

2. Biochemical and Biological Assays
(a) Determination of Inhibitory Action on Acetylcholinesterase.

Cholinesterase (ChE) and acetylcholinesterase (AchE) activity was determined in brain samples prepared according to procedures published previously (J. Neurochem. 50, 1111–1116, 1988). Wistar rat brain was homogenized in 10% (w/v) of ice-cold Tris-buffered saline which comprised 10 mM Tris HCl, pH 7.4, 1 mM ethylenediaminetetraacetic acid, 0.9% (w/v) bovine serum albumin. Homogenates were centrifuged at 10,000 g for 10 minutes at 4° C. Supernatants were decanted and stored in aliquots at −70° C. until required. Protein content was determined by the method of Lowry (J. Biol. Chem. 193, 265–275, 1951).

Enzyme activity was assayed according to the spectrophotometric method of Ellman (Biochem. Pharmacol. 7, 88–95, 1961) with the modifications described by Whittaker (Methods of Enzyme Analysis, 4, 52–74, 1984). Briefly, the assay was carried out at room temperature using 0.1 M phosphate buffer, pH 8.0, containing 0.075 M acetylthiocholine iodide and 0.01 M 5,5-dithio-bis-(2-nitrobenzoic acid) (DTNB). The DTNB was prepared in 0.1 M phosphate buffer, pH 7.0, which contained 0.018 M sodium bicarbonate to ensure stability. The reaction was started by the addition of 100 μg of enzyme preparation to a final assay volume of 3.2 ml, and mixed thoroughly. Progress was monitored spectrophotometrically at 412 nm for a continuous period. A blank was run in conjunction with each assay and differed from the test only in that it contained phosphate buffer in place of acetylthiocholine iodide. AchE was assayed in the presence of ethopropazine, which was prepared in ethanol. The final concentration of ethanol never exceeded 0.3% of the reaction volume and, in separate experiments, no effect on enzyme activity was noted with concentrations as high as 1.5%. BCHE was measured in the presence of $10^{-5}$ M 1,5-bis-(4-trimethylammoniophenyl)pentan-3-one dibromide (62C47), a specific acetylcholinesterase inhibitor which was added to a final concentration of $10^{-5}$ M. All solutions were freshly prepared and protected from light. Acetylthiocholine, DTNB, 62C47 and ethopropazine were obtained from Sigma Chemical Co., St. Louis, Mo. All other reagents were of the highest grade available from routine suppliers.

Results are expressed as mM acetylthiocholine hydrolysed/100 ug protein/min in Table 1. The values were obtained by estimating the slope of the reaction rate with a curve-fitting program, and an absorption coefficient ($\epsilon$) of 1.36 L/mmol/mm (*Methods of Enzyme Analysis*, 4, 52–74, 1984). To facilitate comparison between compounds requiring different solubilization vehicles, the relevant results are expressed as percent of the control value in Table 2.

(b) Reversal of Scopolamine-induced Amnesia of a Passive-avoidance Response.

Animal Maintenance

Postnatal day 80 male Wistar rats (300–350 g) were obtained from the Biomedical Facility, University College, Dublin. These were housed singly in a 12 h light/dark cycle with food and water available ad libitum. Animals employed for neurobehavioral studies were maintained and handled in the test environment for 3 days prior to the commencement of studies. All experimental procedures were approved by the Review Committee of the Biomedical Facility of University College, Dublin and were carried out by individuals who held the appropriate license issued by the Ministry of Health.

Passive Avoidance Paradigm

Animals were trained in a one-trial, step-through, light-dark passive avoidance paradigm. The apparatus consisted of a box measuring 300 mm wide×260 mm deep×270 mm high. The front and top were transparent, allowing observation of behavior inside the apparatus. The box was divided into two compartments, separated by a central shutter which contained a small opening 50 mm wide and 75 mm high. The smaller of the compartments measured 90 mm in width and contained a low power (6 V V) illumination source—the light compartment. The large compartment measured 210 mm in width and was not illuminated. The floor of the training apparatus consisted of a grid of stainless steel bars which could deliver a remotely-controlled, scrambled shock (0.75 mA every 0.5 msec, 5 sec duration) when the animal entered the dark chamber with all four paws. The animals were tested for recall of this inhibitory stimulus prior to sacrifice by placing them into the light compartment and noting their latency to enter the dark compartment. A criterion period of 300 sec was used. The results of this protocol, after administration of saline, scopolamine, test compound, and scopolaine plus test compound, are presented in Table 3.

The present invention has been described in some detail by way of illustration and examples for the purpose of clarity of understanding. It will be obvious that changes and modifications may be produced within the scope of the appended claims.

It is understood that the examples and embodiments described herein are for illustrative purposes only, and that various modifications or changes in light thereof will be suggested to persons skilled in the art and are to be included within the spirit and purview of this application and scope of the appended claims.

TABLE 1

Acetylcholinesterase activity in the presence of benzoquiniolizidines (activity expressed as mM substrate hydrolyzed/min/100 µg protein)

| | Compound concentration | | |
|---|---|---|---|
| Compound | 1.0 mM | 10 µM | 100 nM |
| Example 15 | 0.20 | 2.00 | 2.20 |
| Example 13 | 0.20 | 1.90 | 2.30 |
| Example 17 | 0.80 | 1.90 | 2.00 |
| Example 9 | 0.30 | 2.00 | n.d. |
| Example 18a | 1.70 | 2.10 | 2.30 |
| Example 18b | 1.00 | 1.90 | 2.50 |
| Example 19 | 0.70 | 1.90 | 2.20 |
| Example 20 | 0.30 | 1.40 | 2.10 |
| Tacrine | 0.00 | 0.10 | 1.00 |

TABLE 2

Acetylcholinesterase activity in the presence of benzoquinolizidines (activity expressed as % of control, ± SEM)

| | Compound concentration | | |
|---|---|---|---|
| Compound | 1 mM | 10 µM | 100 nM |
| Example 10 | 42.2 ± 2.9 | 91.6 ± 16.6 | 102 ± 16 |
| Example 14 | 18.6 ± 1.8 | 89.3 ± 0.5 | 78.4 ± 23.6 |
| Example 11 | 2.34 ± 1.91 | 69.6 ± 4.3 | 94.2 ± 22.3 |
| Example 21 | 28.4 ± 9.5 | 74.8 ± 2.8 | 78.8 ± 1.4 |
| Example 23 | 41.7 ± 3.9 | 91.3 ± 2.6 | 105 ± 9 |
| Tacrine | 5.42 ± 0.62 | 7.35 ± 0.05 | 42.1 ± 2.8 |

TABLE 3

Influence of benzoquinolizidines on scopolamine-impaired passive avoidance learning (latency, in seconds)

| | Example 15 10 mg/kg | Example 15 30 mg/kg | Example 13 10 mg/kg | Example 9 10 mg/kg | Example 9 30 mg/kg | Example 9 45 mg/kg |
|---|---|---|---|---|---|---|
| Saline | 600 (6) | 427 ± 130 (5) | 427 ± 121 (6) | 357 ± 94 (6) | 368 ± 84 (6) | 484 ± 67 (6) |
| Scopolamine* | 044 ± 10 (6) | 044 ± 20 (5) | 018 ± 5 (6) | 021 ± 5 (6) | 167 ± 98 (6) | 037 ± 6 (6) |
| Test cpd. + scopolamine* | 148 ± 101 (5) | 132 ± 103 (6) | 048 ± 14 (5) | 104 ± 48 (12)‡ | 258 ± 156 (5) | 322 ± 112 (8)‡ |
| Test cpd. alone | 292 ± 92 (6)† | 188 ± 102 (6) | 410 ± 115 (6) | 459 ± 53 (12) | 529 ± 78 (6) | 340 ± 146 (5) |

TABLE 3-continued

Influence of benzoquinolizidines on scopolamine-impaired passive avoidance learning (latency, in seconds)

|  | Example 9a 10 mg/kg | Example 10 10 mg/kg | Example 14 30 mg/kg | Example 26b 30 mg/kg | Example 34a 30 mg/kg |
|---|---|---|---|---|---|
| Saline | 600 (3) | 508 ± 100 (6) | 531 ± 84 (3) | 600 (4) | 600 (4) |
| Scopolamine* | 030 ± 7 (3) | 041 ± 10 (6) | 017 ± 7 (3) | 119 ± 81 (4) | 199 ± 72 (4) |
| Test cpd. + scopolamine* | 216 ± 260 (2) | 054 ± 20 (6) | 211 ± 238 (3) | 182 ± 163 (4) | 534 ± 76 (3)‡ |
| Test cpd. alone | 328 ± 177 (3) | 592 ± 9 (6) | n.d. | 600 (3) | 559 ± 50 (3) |

*0.8 mg/kg
All values are the mean ± SEM (n).
n.d.: Not determined
†P < 0.05 vs saline;
‡P < 0.05 vs scopolamine alone; Mann Whitney U-Test

We claimed:

1. A compound of the formula:

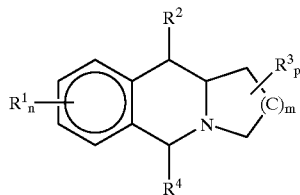

(I)

wherein n=1 to 4, and each $R^1$ independently may be hydrogen, halo, or optionally substituted alkyl or cycloalkyl, aryl, arylalkyl, haloalkyl, haloalkoxy, hydroxy, alkoxy, trifluoromethyl, cyano, carboalkoxy, alkanoyl, aroyl, or alkylsulfonyl;

wherein $R^2=NR_6R_7$, alkylaryl, and $R^6$ and $R^7$ may each independently be hydrogen, optionally substituted alkyl or cycloalkyl, aryl, arylalkyl, alkylaryl, aroyl, alkanoyl, alkylaroyl, or arylalkanoyl, or $NR_6R_7$ may be azetidino, pyrrolidino, or piperidino, wherein p=1 to 6, and $R^3$ is hydrogen, hydroxy, alkoxy, halo, optionally substituted alkyl or cycloalkyl, aryl, arylalkyl, alkylaryl, haloalkyl, haloalkoxy;

wherein $R^4$ is hydrogen, optionally substituted alkyl or cycloalkyl, aryl, arylalkyl, alkylaryl, haloalkyl, or haloalkoxy; and wherein m=2;

with the proviso that the compound is not 11O-acetyl-7,8-dimethoxy-1,3,4,6,11,11a-hexahydro-2H-benzo[b]quinolizin-11-ol.

2. A compound of formula 2 or 3 below:

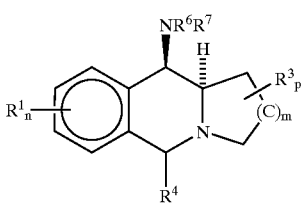

(2)

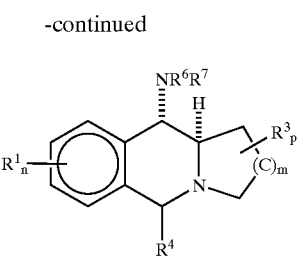

(3)

wherein n=1 to 4, and each $R^1$ independently may be hydrogen, halo, or optionally substituted alkyl or cycloalkyl, aryl, arylalkyl, haloalkyl, haloalkoxy, hydroxy, alkoxy, trifluoromethyl, cyano, carboalkoxy, alkanoyl, aroyl, or alkylsulfonyl;

wherein $R^6$ and $R^7$ may each independently be hydrogen, optionally substituted alkyl or cycloalkyl, aryl, arylalkyl, alkylaryl, aroyl, alkanoyl, alkylaroyl, or arylalkanoyl, or $NR_6R_7$ may be azetidino, pyrrolidino, or piperidino;

wherein p=1 to 6, and $R^3$ is hydrogen, hydroxy, alkoxy, halo, optionally substituted alkyl or cycloalkyl, aryl, arylalkyl, alkylaryl, haloalkyl, haloalkoxy;

wherein $R^4$ is hydrogen, optionally substituted alkyl or cycloalkyl, aryl, arylalkyl, alkylaryl, haloalkyl, or haloalkoxy; and wherein m=2.

3. A compound according to claim 2 wherein the compound has structure 2, $R^1$ is H, $R^3$ is H, $R^4$ is H, $R_6$ is H, and $R^7$ is methyl.

4. A compound according to claim 2 wherein $R^1$ is H and n is 4, $R^3$ is H, $R^4$ is H, $R^6$ is H, and $R^7$ is benzyl.

5. A compound according to claim 2 wherein $R^1$ is 9-methoxy and n is 1, $R^3$ is H, $R^4$ is H, $R^6$ is H, and $R^7$ is methyl.

6. A compound according to claim 2 wherein $R^1$ is 9-methoxy and n is 1, $R^3$ is H, $R^4$ is H, $R_6$ is H, and $R^7$ is phenylmethyl.

7. A compound according to claim 2 wherein $R^1$ is 8-chloro and n is 1, $R^3$ is H, $R^4$ is H, $R^6$ is H, and $R^7$ is methyl.

8. A compound according to claim 2 wherein the compound has structure 2.

9. A pharmaceutical composition comprising at least one compound of any one of claims 1 to 8, in an amount effective for treating a disease state or controlling symptoms in a mammal suffering from memory impairment, as a result of Alzheimer's disease, senile dementia or similar conditions, in combination with one or more pharmaceutically acceptable carriers.

10. A method for treating a disease state or controlling symptoms in a mammal suffering from memory impairment, as a result of Alzheimer's disease, senile dementia or similar conditions, comprising administering to a subject in need of such treatment an effective amount of at least one compound of any one of claims 1 to 8.

* * * * *